United States Patent
Azizian

(10) Patent No.: US 7,329,547 B2
(45) Date of Patent: Feb. 12, 2008

(54) FT-NIR FATTY ACID DETERMINATION METHOD

(75) Inventor: Hormoz Azizian, Oakville (CA)

(73) Assignee: NIR Technologies, Inc., Oakville, Ontario (CA)

( * ) Notice: Subject to any disclaimer, the term of this patent is extended or adjusted under 35 U.S.C. 154(b) by 0 days.

(21) Appl. No.: 11/134,442

(22) Filed: May 23, 2005

(65) Prior Publication Data

US 2005/0250213 A1 Nov. 10, 2005

Related U.S. Application Data

(63) Continuation-in-part of application No. 10/840,277, filed on May 7, 2004, now abandoned.

(51) Int. Cl.
*G01N 33/92* (2006.01)
*G01N 21/62* (2006.01)

(52) U.S. Cl. ............... 436/71; 436/20; 436/161; 436/164; 436/171; 356/51; 356/300; 356/317

(58) Field of Classification Search ........... 436/8, 436/13, 20, 23, 71, 161, 164, 171, 173; 356/51, 356/300, 306, 317, 326, 451, 432, 433
See application file for complete search history.

(56) References Cited

U.S. PATENT DOCUMENTS

2004/0092803 A1* 5/2004 Azizian et al. ............ 600/310

2005/0029457 A1 2/2005 Long et al.

OTHER PUBLICATIONS

Li et al. JAOCS, vol. 77, No. 10, 2000, pp. 1061-1067.*
Mossoba et al. "Official Methods for the Determination of Trans Fat", AOCS Press, 2003.*
Li et al. Rapid Determination of cis and trans Content, Iodine Value, and Saponification Number of Edible Oils by Fourier Transform Near-Infrared Spectroscopy. JAOCS, vol. 76, No. 4, 1999, pp. 491-497.*
Azizan et al., "Quantification of trans fatty acids in food products by GC, ATR-FTIR and FT-NIR methods," Lipid Technology, vol. 16, No. 10, Oct. 2004.
Mailer, "Rapid Evaluation of Olive Oil Quality by NIR Reflectance Spectroscopy", JAOCS, vol. 81, No. 9 (2004).
Cox, R. et al., "A Comparison of Fourier Transform Mid Infrared and Near Infrared Technologies for Trans Analysis" Abstracts 93rd AOCS Annual Meeting & Expo, May 5-8, 2002 . . . .

* cited by examiner

*Primary Examiner*—Maureen M. Wallenhorst
(74) *Attorney, Agent, or Firm*—Jones Day

(57) ABSTRACT

A method for the rapid analysis of the fatty acid components present in a fat and/or oil-containing material is provided wherein the levels and types of fatty acids present in a sample are determined using Fourier Transform Near Infrared (FT-NIR) spectroscopy. The FT-NIR technique is developed by preparing a calibration matrix based on FT-NIR and Gas Chromatography (GC) analysis of known standards, and subsequently using the calibration matrix to analyze the FT-NIR spectral data obtained from a sample to be tested.

24 Claims, 8 Drawing Sheets

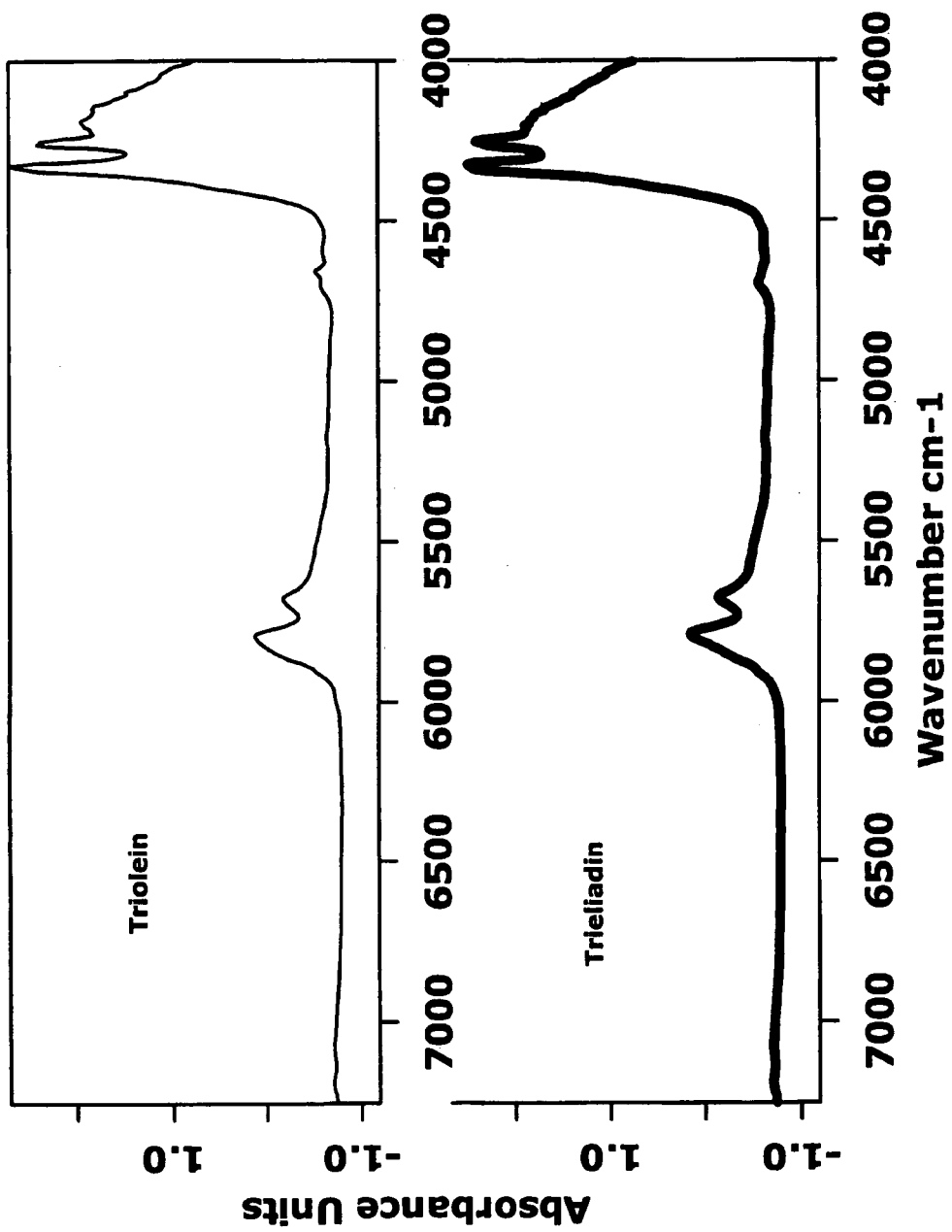
Figure 2  FT-NIR Absorption Spectra for Trieliadin and Triolein

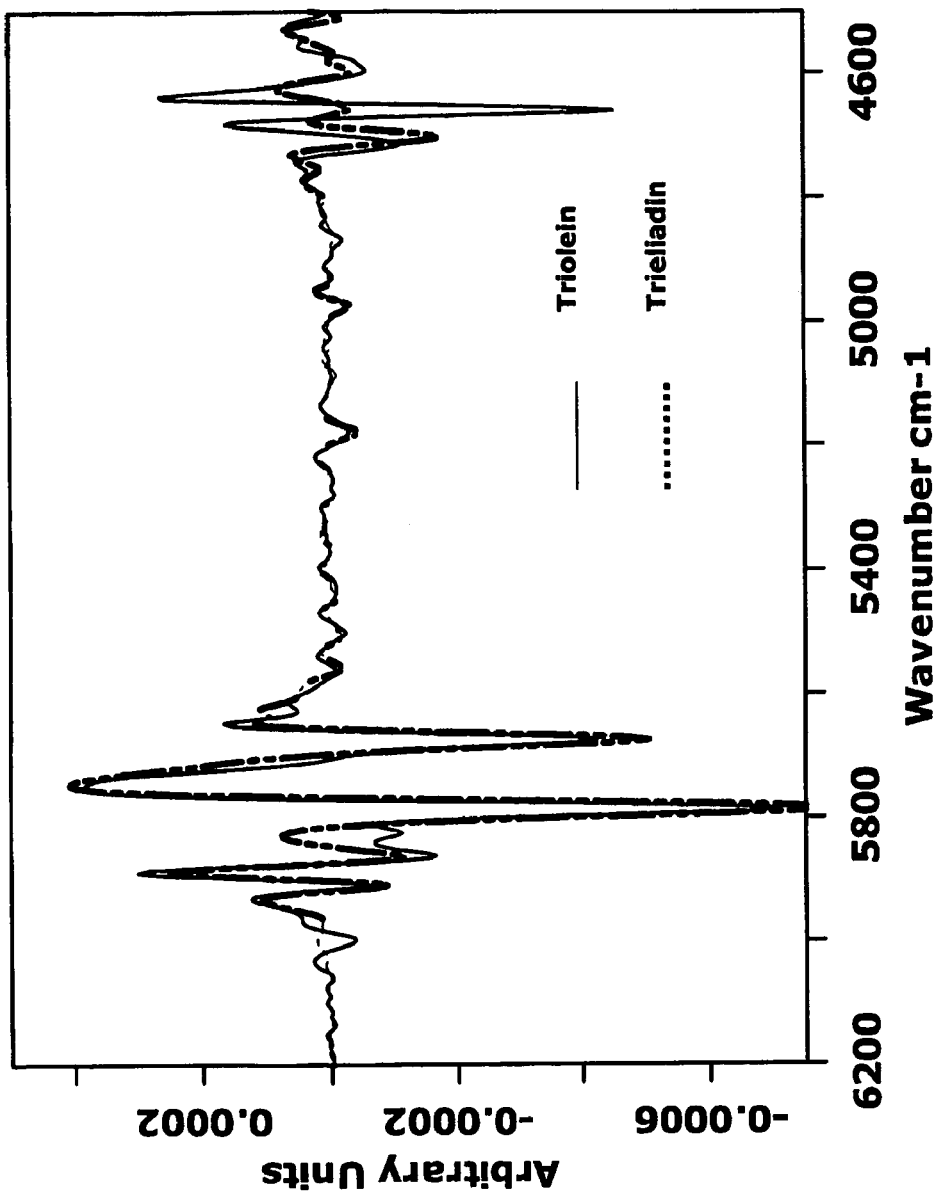
Figure 3 Second derivative comparison of Triolein and Trielaidin

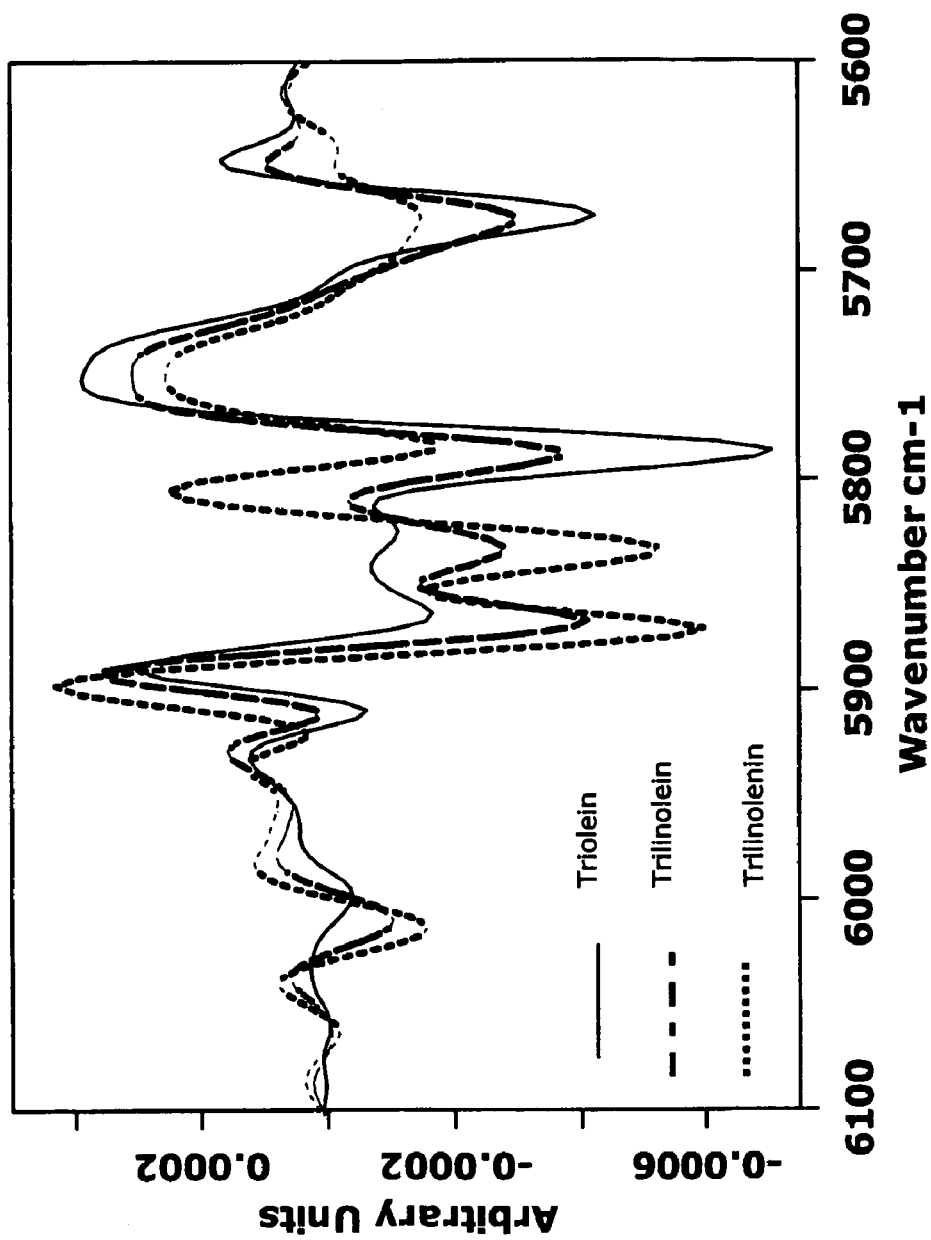
Figure 4   Second derivative comparison of Triolein, Trilinolein, and Trilinolenin

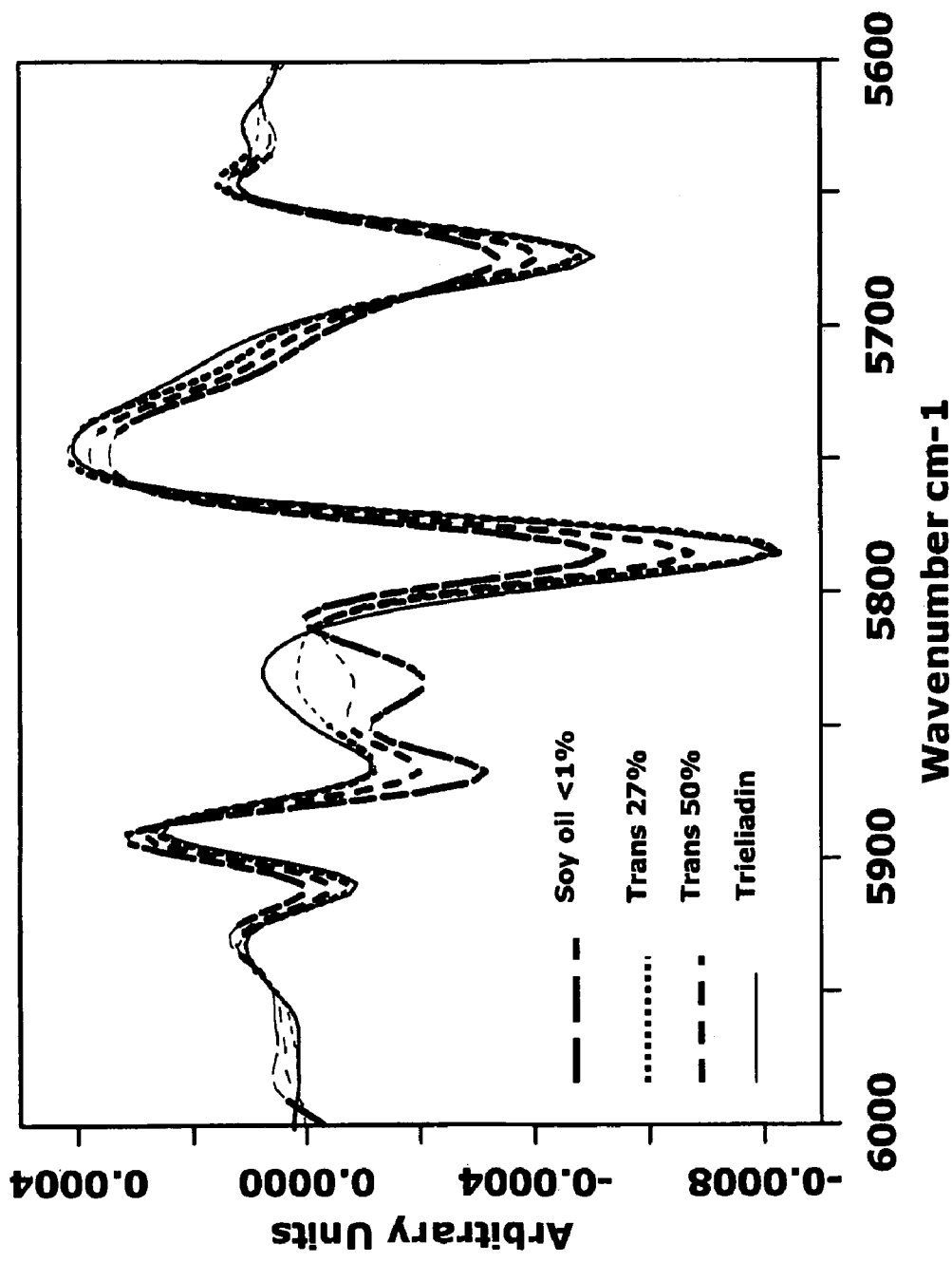
Figure 5  Second derivative comparison of Partially Hydrogenated Soy Oil and Trieliadin

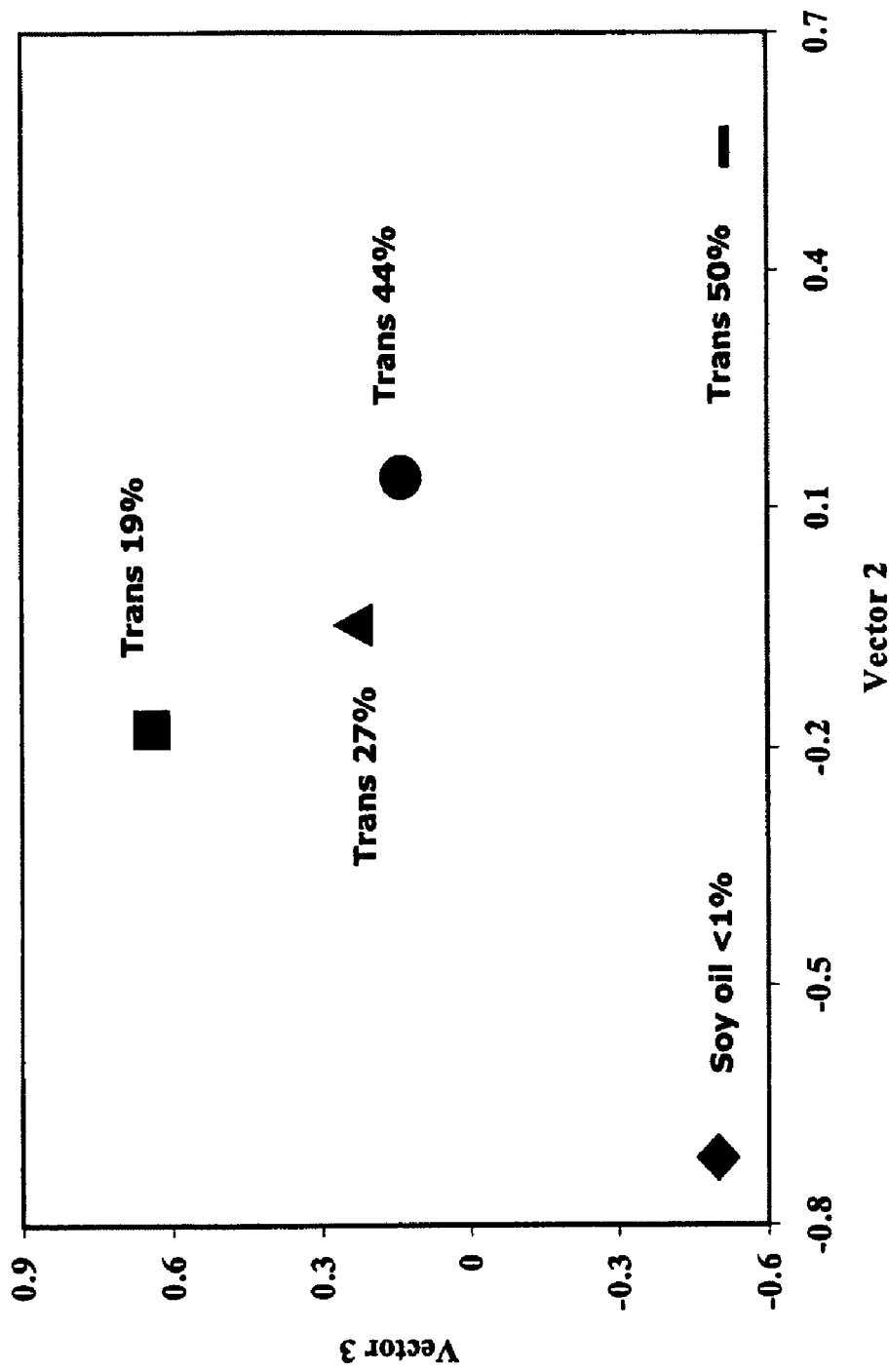
Figure 6  Factorized Analysis of Partially Hydrogenated Soy Oils

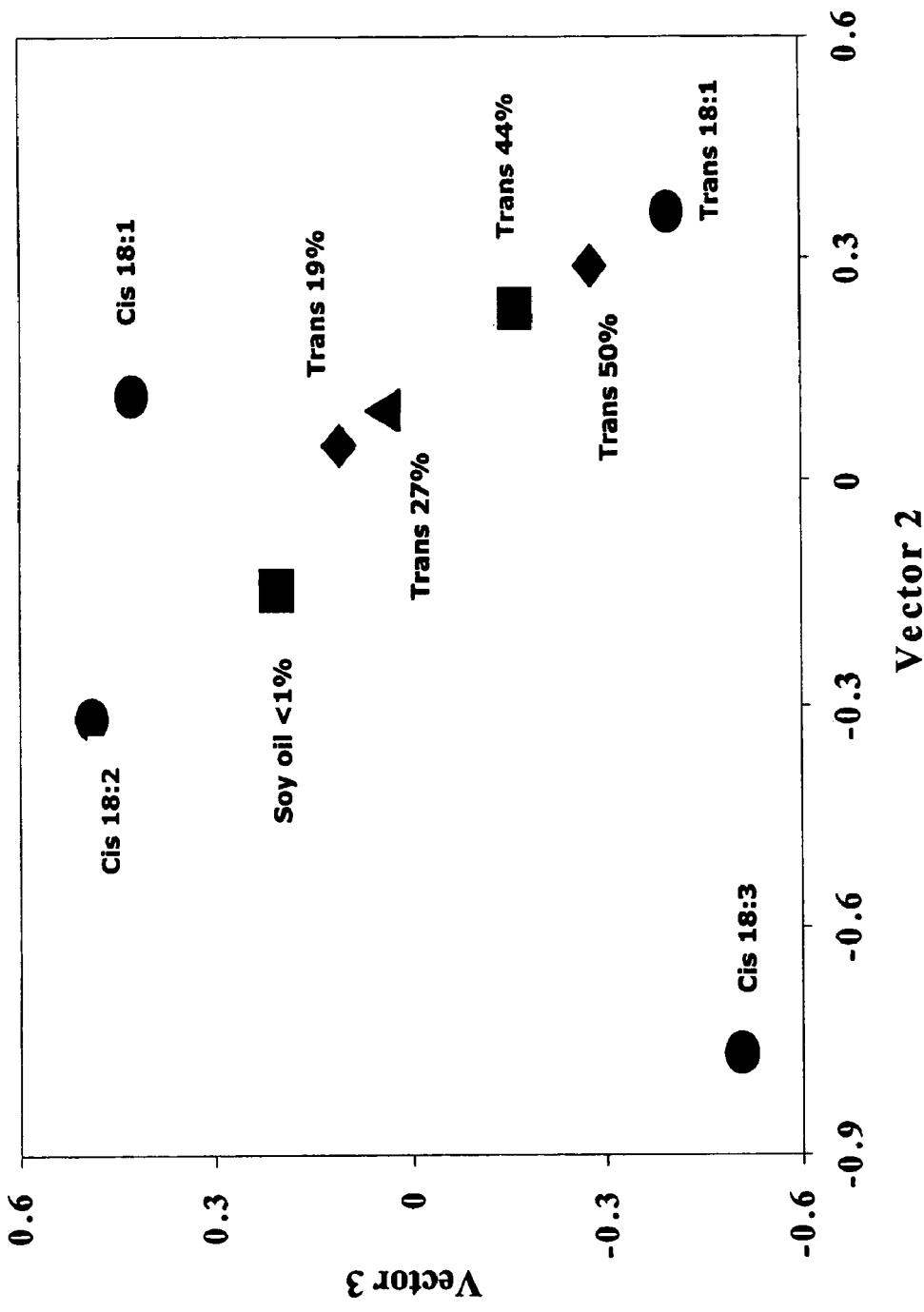
Figure 7 Factorized Analysis of Partially Hydrogenated Soy Oils and Triglycerides

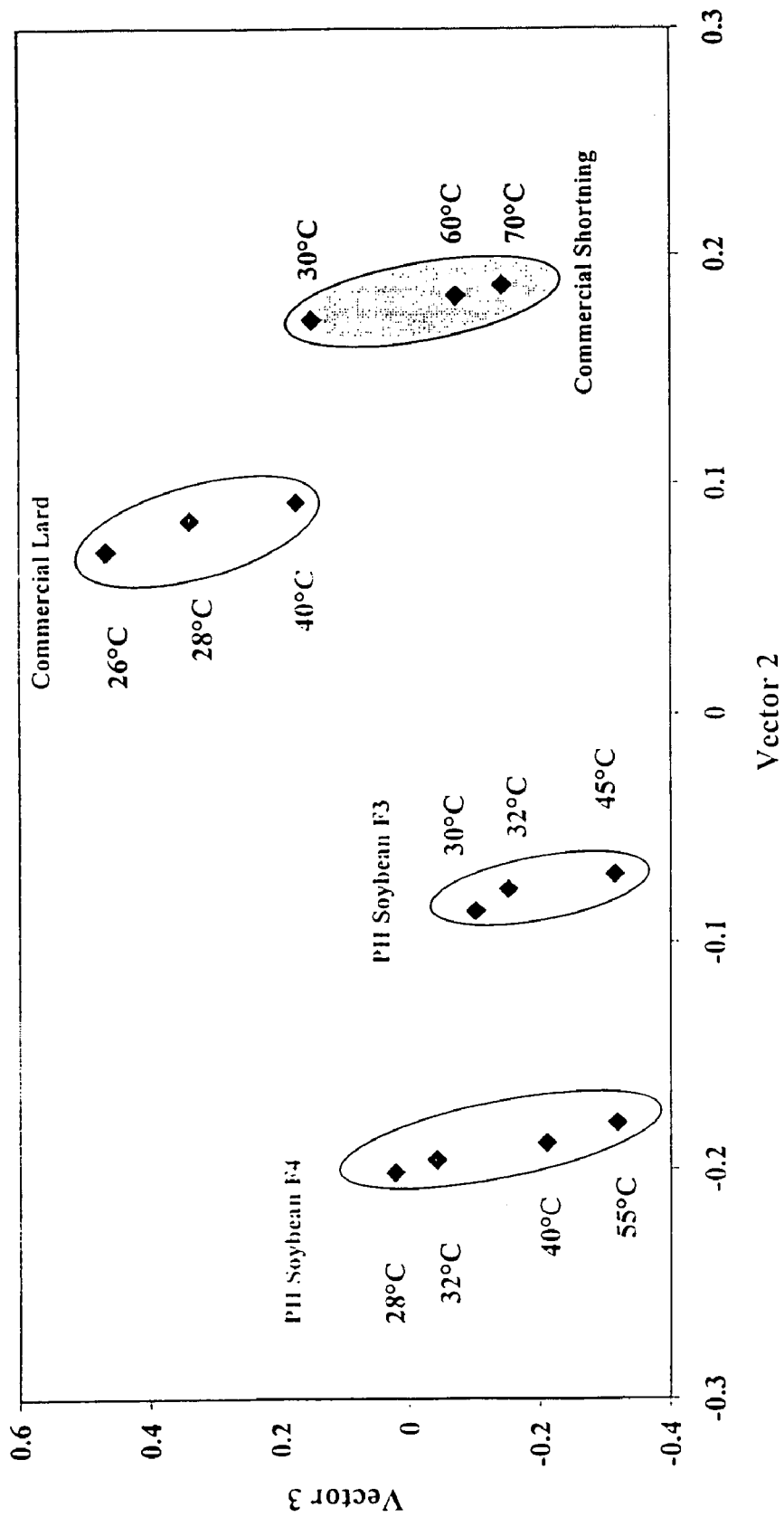
Figure 8 Effect of Temperature on the Identification of Oils and Fats
Caption for figure: PH Soybean F3 or F4 = Partially Hydrogenated Soybean Oil Sample F3 or F4

FT-NIR FATTY ACID DETERMINATION METHOD

CROSS REFERENCE TO RELATED APPLICATIONS

This application is a continuation-in-part application of U.S. patent application Ser. No. 10/840277, filed May 7, 2004 now abandoned. The entirety of this document is incorporated herein by reference.

FIELD OF THE INVENTION

The invention relates to a method for the measurement of fatty acid content in a selected material by the use of radiation in the near infrared region of the light spectrum.

BACKGROUND OF THE INVENTION

Recently there has been increasing interest in the determination of the quantity and type of fatty acids present in the oils and fats which are used in the food, and other industries. For example, recently government and health organizations have called for, or imposed regulations on the amount and type of fatty acids contained in food products. Also, food suppliers are increasingly being mandated to provide information on the quantity and types of fatty acids contained within their products. This is particularly true for materials termed as "trans fatty" acids, as discussed hereinbelow.

Fats and oils are made of a complex mixture of a chemically similar group of compounds known as fatty acids. However, the composition of the fats and oils present in a given material is largely dependent on the source of the material. For example, vegetable oils are composed of mainly palmitic, palmitoleic, stearic, oleic, linoleic and linolenic acids. On the other hand, commercially manufactured "shortening" materials may contain over 30 different fatty acids including numerous trans fatty acids.

There are several different types of fat materials. Some fats occur naturally, while others are only attainable by diet. Briefly, the types of fat are saturated fats, unsaturated fats, phospholipids and triglycerides. Saturated fats are commonly found in animal fat products such as butter, lard and animal meats. Unsaturated fats, are divided into two groups, mono or poly unsaturated fats. An example of a monounsaturated fat is triolein, or its associated fatty acid, Oleic acid, which is the main component of olive oil. Polyunsaturated fats are essential fatty acids and are only attainable through diet. Examples of polyunsaturated fats are linoleic acid, linolenic, arachidonic acids, eicosapentaenoic acid (EPA) and decosahexaenoic acid (DHA). These fatty acids may be found in soy bean oil, peanut oil, corn oil, and fish oil, or more generally, oils extracted from fish, to name a few.

Phospholipid fats, the most common of which is lecithin, are an important common component of all cell membranes.

Triglycerides, are composed of three fatty acids attached to glycerol molecule and are, for example, the storage form of fat that occurs when humans eat calories in excess of their energy needs.

The so-called "trans fatty acids" are carboxylic acids with a long hydrocarbon chain in which the isolated double bond occurs in the "trans" configuration. It should be noted that most of the unsaturated sites in natural fats and oils from plant or animal origins generally occur in the "cis" double bond configuration. A small amount of "trans" fat is found naturally in ruminant fat, but is most commonly introduced into food or other materials during partial hydrogenation of, for example, vegetable oils. Levels of trans fat of up to 50% have been reported in products produced from partially hydrogenated vegetable oil.

This is of concern since recent studies have questioned the long term health issues related to the consumption of trans fatty acids. For example, studies have now suggested a link between trans fatty acid consumption and coronary heart disease. As such, there is increasing interest in determining the level of trans fatty acids in a material, and, more generally, in determining the quantity and type of all oils and/or fatty acids present in materials, and in particular, the levels and types of these materials which is present in food. Further, recent evidence has also suggested that there is a beneficial effect provided by EPA or DHA with respect to coronary heart disease, and it would therefore be useful to determine the levels of these, or other, beneficial materials.

Further, Omega-3 longer-chain (LC) polyunsaturated fatty acids (PUFAs), which are available mainly from fish oil in the form of triglycerides, have shown to have positive effect in reducing coronary heart disease (CHD). Since the body is unable to synthesize some of these Omega-3 (LC) PUFAs and they are required for improved health, these fatty acids have been termed 'essential' fatty acids. Two main Omega-3 (LC) PUFAs contained in fish oil are Eicosapentaenoic acid (EPA) and Decosahexaenoic acid (DHA), described hereinabove, and currently they are analyzed by gas chromatographic methods. As the health benefits of these fatty acids have increased over the last decade so has the commercial production and testing requirements.

Currently, the level and type of oils and/or fatty acid, and the determination of trans fatty acid, is performed using capillary gas chromatography (GC) analysis, or by use of infrared (IR) spectroscopic techniques, as described in a monograph from the American Oil Chemists' Society ("Official Method for the Determination of Trans Fat", Mossoba et al., AOCS Press, 2003), the contents of which is incorporated herein by reference. While these techniques provide the necessary information, they suffer from some inherent difficulties.

First, the GC technique requires that representative samples be collected, processed and prepared for analysis (sometimes using toxic materials) over several hours, and then analyzed using a GC procedure that can take more than 45 to 60 minutes, or longer, to complete. As such, the GC technique can require several hours of a trained GC operator's time in order to finally prepare, analyze and report the results from the samples. In a production situation, the time and cost of this technique can be prohibitive.

This technique is also described by Satchithanandam et al. in "Trans, Saturated, and Unsaturated Fat in Foods in the United States Prior to Mandatory Trans-Fat Labeling", Lipids, Vol. 39, No. 1 (2004).

Other chromatography techniques including silver ion Thin Liquid Chromatography (TLC-GC), and High Performance Liquid Chromatography (HPLC) are also known, but these techniques suffer from the same problems as the above mentioned GC techniques.

With the IR technique, a sample of the material to be tested is exposed to an Infrared light source, and the transmission or reflectance of the Infrared light is measured so that the amount of absorption can be determined. In traditional mid-infrared spectroscopy, the sample is progressively exposed to IR wavelengths so that an absorption spectrum is produced which can be compared to known standards for both absorption wavelength, and for the percentage of absorption. As such, the type of fatty acid or oil can be determined, and the amount present can be calculated.

This mid-infrared spectroscopy technique has been used since the 1940's for determining the trans content of fats and oils. However, it is also time consuming to prepare the sample for testing, and is subject to errors introduced by absorption of other materials such as water or the like. As such, using mid-infrared dispersive spectrometers that use prisms or diffraction gratings to resolve the infrared light into its component wavelengths, does not typically have the required accuracy necessary for precise quantitative analysis.

The advent of Fourier transform infrared spectroscopy (FTIR) has, however, led to improvements in compensating for absorption by other materials, and greatly improves the sampling time, and accuracy. In an FTIR machine, a pulse of infrared radiation is emitted, and an interferometer allows the essentially simultaneous detection of all of the reflected or transmitted component wavelengths of the mid-infrared region (4000 to 600 cm$^{-1}$). A Fourier transformation calculation is then performed on the interferometer output to determine a spectrum which is essentially identical to the spectrum obtained by variation of the frequency.

Near Infrared (NIR) spectroscopy is a similar technique to infrared spectroscopy, wherein radiation from only the near infrared region is used. However, the interest in NIR for the analysis of various chemicals and other materials stems from a number of factors. For example, absorptions in the near infrared region arise from vibrational transitions to the second or higher energy states. Because of the very low probability of such transitions, absorption intensities are typically several orders of magnitude below those of the corresponding fundamental vibrations in the infrared and/or ultraviolet (UV) regions. Consequently NIR has improved sensitivity in the analysis of species present at low concentrations over conventional IR techniques.

Also, near infrared spectroscopy has the advantage that aqueous solutions can be readily analyzed without significant interference from water absorption since water does not significantly absorb the NIR radiation. Further NIR allows for the use of quartz or glass materials to be used in the construction of the NIR apparatus or in the sampling equipment, which materials cannot be used in traditional IR devices.

Further, the intense absorption of near infrared radiation at only selected wavelengths by a species, allows the NIR radiation to penetrate a sample sufficiently in order to be useful in the analysis of thicker samples.

As with the FTIR technique, Fourier transformation of the NIR spectrum (FT-NIR) provides improved results, wherein the FT-NIR instrument again makes use of an interferometer to encode data from the whole spectral range simultaneously. The interferometer, and preferably a Michelson interferometer, is thus used to produce a signal of a lower frequency than the frequency emitted from the NIR source. The lower frequency contains the same information as the original radiation signal, but its output is supplied at a speed slow enough for detection by a detector. The resultant output of the interferometer is an interferogram of all wavelengths emitted by the source.

A computer then performs a Fourier Transform on the interferogram and generates a frequency domain trace specific to the tested material.

FT-NIR spectroscopy has certain advantages over the traditional IR or NIR spectroscopy, in which the response of a sample to light is measured by scanning sequentially over a range of wavelengths. Primarily, however, the FT-NIR technique is rapid, less energy limited than using FTIR machines, can use glass or quartz cells, and can use sensitive detectors contained in more convenient forms. For example, FT-NIR devices are available which use fibre optics to transmit the NIR radiation to hand-held devices which can be merely inserted into the material to be tested. Alternatively, low cost glass sampling equipment can be used when analyzing the selected material.

FT-NIR spectroscopy has been previously used to determine the amounts of cis, trans, the relative degree of unsaturation or iodine values (IV), and the weight average molecular weight of saponification number (SN) parameters of edible fats and oils. This is described by Li et al. in "Rapid determination of cis and trans content, iodine value, and Saponification Number of Edible Oils by Fourier Transform Near-Infrared Spectroscopy", JAOCS, Vol. 76, No. 4 (1999). However, this technique relies on establishing a series of known materials by using an analysis based on an FTIR technique, and using this information to establish a calibration curve for use with the FT-NIR device. However, this technique relies on the accuracy of the underlying FTIR technique.

A similar technique is described by Li et al. in "Trans Determination of Edible Oils by Fourier Transform Near-Infrared Spectroscopy", JAOCS, Vol 77, No. 10 (2000), in which FT-NIR is used to measure trans fat content based on a calibration curved generated by testing a series of known samples using a single bounce, horizontal attenuated total reflectance, mid Infrared based technique.

While these techniques have some advantages over the prior art methods, they both rely on establishing a calibration curve (or matrix) based on a mid-FTIR technique, with its inherent analysis difficulties and accuracy limitations. To overcome these difficulties, it would be advantageous to provide a method of quantitative measurement of the amounts and types and/or categories of the fatty acid content in a material containing fats and oils, using a method with improved accuracy while maintaining a technique having good flexibility of use.

SUMMARY OF THE INVENTION

Accordingly, it is a principal advantage of the present invention to provide a rapid method for the quantitative analysis of the fatty acid content of a material containing fats and/or oils.

It is a further advantage of the present invention to provide a method in which the tested material is a food product.

It is a still further advantage of the present invention to provide a method wherein the analytical technique is based on a more accurate instrument calibration matrix.

The advantages set out hereinabove, as well as other objects and goals inherent thereto, are at least partially or fully provided by the method for fatty acid analysis in a material, of the present invention, as set out herein below.

As such, the present invention provides a method for the determination of the fatty acid type and/or content of a fat or oil component of a test sample material, which method comprises preparation of a calibration matrix using a fatty acid reference analytical technique adapted to identify the type and quantity of fatty acids in a baseline reference material, and relating the results obtained to the spectral data obtained from an FT-NIR analysis of said baseline reference material;

analysing a test sample material using an FT-NIR technique to obtain FT-NIR spectral data for said test sample material; and relating said FT-NIR spectra data of said test sample material to said calibration matrix in order to determine a value for the fatty acid content of any or all of the fatty acids present in said test sample material.

The fatty acid reference analytical technique is any analytical technique which can directly, or indirectly provide specific information on the type and quantity of the fatty acid components of a fat or oil. Preferably, the fatty acid reference analytical technique is based on a GC (gas chromatography) procedure, and can therefore including such techniques as GC, GC Silver Ion, GC-HPLC (High Performance Liquid Chromatography), GC-TLC (Thin Layer Chromatography), GC-MS (Mass Spectrometry)or the like, or any other suitable GC technique known to those skilled in the art.

As such, the calibration matrix is preferably prepared using a technique based on data obtained by GC and FT-NIR analysis of selected baseline materials.

Accordingly, the present invention also provides a method for the determination of the fatty acid type and/or content of a fat or oil component of a test sample material, which method comprises:

identifying a series of baseline materials having a similar composition to that of a test sample material, and containing at least one form of fatty acid having a reflectance or transmission characteristic corresponding to a narrow wave band of light in the near-infrared region of the spectrum;

analysing said baseline materials using a GC technique to determine the fatty acid composition of each of said baseline materials;

analysing said baseline materials using an FT-NIR technique to produce FT-NIR spectra data for each of said baseline materials;

establishing a calibration matrix to relate the FT-NIR spectra data to the results determined from said GC technique for any or all of said fatty acids identified by said GC technique;

analysing a test sample material using said FT-NIR technique to produce NIR spectral data for said test sample material, and relating the spectral data from said FT-NIR technique to said calibration matrix to determine a value for the fatty acid content of any or all of the fatty acids present in said test sample material.

The procedure of the present invention is particularly adapted for the rapid determination of the fatty acid compositions of various materials containing fats and oils, and is particularly adapted for the rapid determination of trans fatty acid levels of various materials, or analysis of other materials such as, for example, Omega-3(LC) PUFA's.

DETAILED DESCRIPTION OF THE INVENTION

The invention provides a method for determining the fatty acid content of a selected material using a Fourier Transform Near infrared (FT-NIR) spectrometer and using various calculations.

The FT-NIR spectroscopy has a much higher resolution and accuracy level than Near Infrared (NIR) spectrometers. The FT-NIR spectrometer has a spectral resolution of 0.3 nm (2 $cm^{-1}$ at 8000 $cm^{-1}$) whereas other grating or filter instruments are between 2 nm (5 $cm^{-1}$ at 5000 $cm^{-1}$) to 10 nm (25 $cm^{-1}$ at 5000 $cm^{-1}$). Further, dispersive instruments operate in a frequency domain whereas the Fourier Transformed NIR Infrared (FT-NIR) may be operated in the frequency domain or a time domain. The advantage of operating in a time domain allows for faster results.

Near infrared wavelengths of light are absorbed by species due to distinctive molecular vibrations and low level electronic excitations. Many molecules, particularly molecules of biochemical interest, have characteristic "fingerprint" absorption spectra in the near infrared.

While there is no exact definition of the frequency range related to the term "near infrared", generally, the term is used to define the range of frequencies between 4000 and 14000 $cm^{-1}$ (2.5 to 0.7 microns) wavenumber, and the technique of the present invention is applicable over this general range. However, preferably, the FT-NIR technique of the present invention is practiced within the range of 4300 to 9000 $cm^{-1}$ (2.2 to 1.1 microns), and even more preferably, the technique is practiced within the range of 5400 to 9000 $cm^{-1}$ (1.7 and 1.1 microns).

In use, the sample material is placed adjacent to the output of the interferometer and the detector. The sample absorbs radiation of specific wave lengths. The unabsorbed radiation is reflected (or otherwise transmitted) back to the detector and recorded as an interferogram. The interferogram is then transformed into a single channel spectrum by Fourier Transformation. The background spectrum is then used to calculate the transmission or absorption of the sample. After an interferogram has been collected, a computer performs a Fast Fourier Transform (FFT), which results in a frequency domain trace (i.e. intensity vs wavenumber). The detector used in an FT-NIR instrument must respond quickly because intensity changes are rapid (the moving mirror moves quickly). To achieve a good signal to noise ratio, many interferograms are obtained and then averaged. This can be done in less time than it would take a dispersive instrument to record one scan.

The advantages of the Fourier Transform Near Infrared Spectrometers over Dispersive Near Infrared Spectrometers include:

Improved frequency resolution;

Improved frequency reproduceablity;

Higher energy throughput;

Faster operation computer based (allowing storage of spectral facilities for processing spectra); and Easily adapted for remote use.

As such, the FT-NIR technique is superior to any similar techniques using FTIR or dispersive IR techniques.

In the present application, the term "test sample material" refers primarily to a food product, and as such, the present application is primarily directed to the use of this technique for the determination of fatty acid content and composition in food products. However, the skilled artisan will be aware that this technique might also be used in a wide variety of applications where measurement of fatty acid composition is desired. Accordingly, while the present application is described with particular reference to the food industry, the skilled artisan would be aware that the present application is equally applicable in other non-food-related applications.

It is to be noted that the skilled artisan will be well aware of the GC techniques used to determine the types and amounts of the fatty acids found in a given sample, as described in, for example the AOCS monograph described hereinabove. As such, the GC technique will not be described in any detail, but it is sufficient to state that a skilled artisan trained in the use of GC equipment would readily be able to produce the necessary GC data using readily available techniques and methods.

This data, however, once obtained by the GC technique, would form the basis of the calibration matrix developed for the particular material, or group of related materials, to be tested.

The baseline materials are preferably materials which are similar in composition (particularly with respect to the type of fatty acid) to the test sample material but having a range of fatty acid levels. As such, a range of fatty acid levels can be determined using the GC technique. The range of fatty acid levels might be prepared by adding or removing known amounts of fatty acid materials to some of the baseline materials.

Alternatively, the baseline materials might be materials which are prepared from blends of known materials in order to simulate the test sample composition with respect to any or all of the fatty acid components.

Once the baseline materials have been selected and analyzed using the GC technique, they are then tested using the FT-NIR technique. Again, the skilled artisan will be well aware of the use of suitable commercial FT-NIR devices, and the use of these devices will not be described in detail. These FT-NIR devices are readily available.

Preferably, however, the FT-NIR device has fibre optic probe through which the near infrared radiation can be transmitted, and a detector to which the transmitted infrared radiation can be directed (as a transmitted, reflected or transflected emission). The FT-NIR device is then capable of analyzing the transmitted or reflected NIR radiation using a Fourier Transform technique in order to determine the spectral data for the sample material. This spectral data may be in the form of a chart showing the entire NIR spectra, but might also be data collected from specific, selected NIR frequencies. As such, the intensity of the collected radiation is compared in specific frequencies to the wave band obtained from testing the baseline materials having a known fatty acid composition. By comparison of the spectral data, the reflectance and/or transmission characteristics of the baseline materials,—with known fat composition, can be compared to the values obtained from the test sample material. As a result of this comparison, a calibration matrix can be prepared for a selected test material, or group of materials.

Comparison of the spectral data can be based on the actual reflectance or transmittance data, but can also be based on mathematically modified values of the spectral data. This can include, for example, determination of second derivative values, and comparison based on these second derivative values. Use of these types of mathematically modified values can improve the ability to distinguish one material over another.

For example, a margarine producer can prepare a calibration matrix from a series of baseline margarine samples all of which might have fatty acid compositions similar to the fatty acid composition of the margarine test sample. It will be clear that the more baseline materials that are analyzed by the GC and FT-NIR techniques, the better the calibration matrix will become.

Using the calibration matrix, the FT-NIR technique is used on a margarine test sample. This can be conducted rapidly during production by use of a probe inserted into the production stream, or in a sample of material collected from the production stream. It is possible that the test sample might require pre-treatment including, for example, heating to melt the test material, or the like. Commonly however, the test sample is used as is.

Using the FT-NIR probe, the spectral data for the test material is rapidly obtained, and then compared to the calibration matrix applicable for that test material, in order to determine values for the types and amounts of fatty acids present in the test material. As a result, the user is able to determine the fatty acid composition of the test sample in less than a matter of minutes versus the time of several hours required for the GC or, the user is able to determine the fatty acid composition of the test sample with more specificity than possible with prior art IR techniques. Once a reference library has been constructed, typically, the FT-NIR scanning and analysis of the test sample material is conducted in less than 5 minutes, and more preferably, is conducted in less than 2 minutes.

The test sample material is preferably a food material containing or comprising a fat or oil having a fatty acid component. This can include materials such as oils such as vegetable oils, soy oils, flax oils, fish oils or oils extracted from fish, or the like, shortening, lards, mayonnaise, salad dressings, cookies, baked goods, crackers, potato chips, or a wide range of other food products. However, the test sample material can be any material having a fatty acid component, which might include analysis of living tissue such as human tissue, fish, or other non-human mammal tissue.

Preparation of the calibration matrix is known to those skilled in the art, and may consist, at a simple level, as being a straight line comparison of the spectral data at a selected frequency to the spectral data obtained from the range of baseline materials. However, typically, the calibration matrix will be somewhat more complex mathematical model which can be used in order to compare a series of spectral data (e.g. frequency and transmittance and/or reflectance data). Using these mathematical models, a calibration matrix is prepared which is capable of determining the types and/or the amounts of a number of fatty acids which may be present in a selected test material.

The mathematical models used to prepare the calibration matrix can be based on statistical analysis of the spectral data which have been compared to the GC data, in order to analyse complex chemical mixtures and solutions. Typically, the user will start by constructing a data matrix from the GC data and FT-NIR spectra for a set of baseline materials. The calibration matrix is then prepared by mathematical analysis of the data matrix. Suitable mathematical approaches for preparation of the calibration matrix can include, for example, mathematical techniques such as multiple linear regression (MLR), principal component regression (PCR), and partial least squares regression (PLSR), although other methods can be adopted.

The calibration matrix can be limited to only a selected type of material (e.g. margarine) having a limited number of fatty acid types, and limited range of fatty acid levels. As such, a less complex calibration matrix is required. However, as more types of materials are analysed or otherwise encountered, with different fatty acid types and with wider ranges of fatty acid levels, the calibration matrix will, by necessity become more complex. The skilled artisan, however, will be able to determine the complexity of the calibration matrix required for a selected application. As such, the skilled artisan would be able to select a calibration matrix "library" appropriate for the type of materials to be tested.

The various features of novelty which characterize the invention are pointed out with more particularity in the claims annexed to and forming a part of this disclosure. For a better understanding of the invention, its operating advantages and specific objects attained by its use, reference should be made to the accompanying drawings, examples, and descriptive matter in which there are illustrated and described preferred embodiments of the invention.

BRIEF DESCRIPTION OF THE DRAWINGS

Embodiments of this invention will now be described by way of example only in association with the accompanying drawings in which:

FIGS. 2 to 5 are FT-NIR spectral data taken from a variety of materials;

FIGS. 6 and 7 show factorized analysis results of different materials; and

FIG. 8 is a figure showing the temperature effect on identification of materials.

DETAILED DESCRIPTION OF THE PREFERRED EMBODIMENTS

Figure 1:
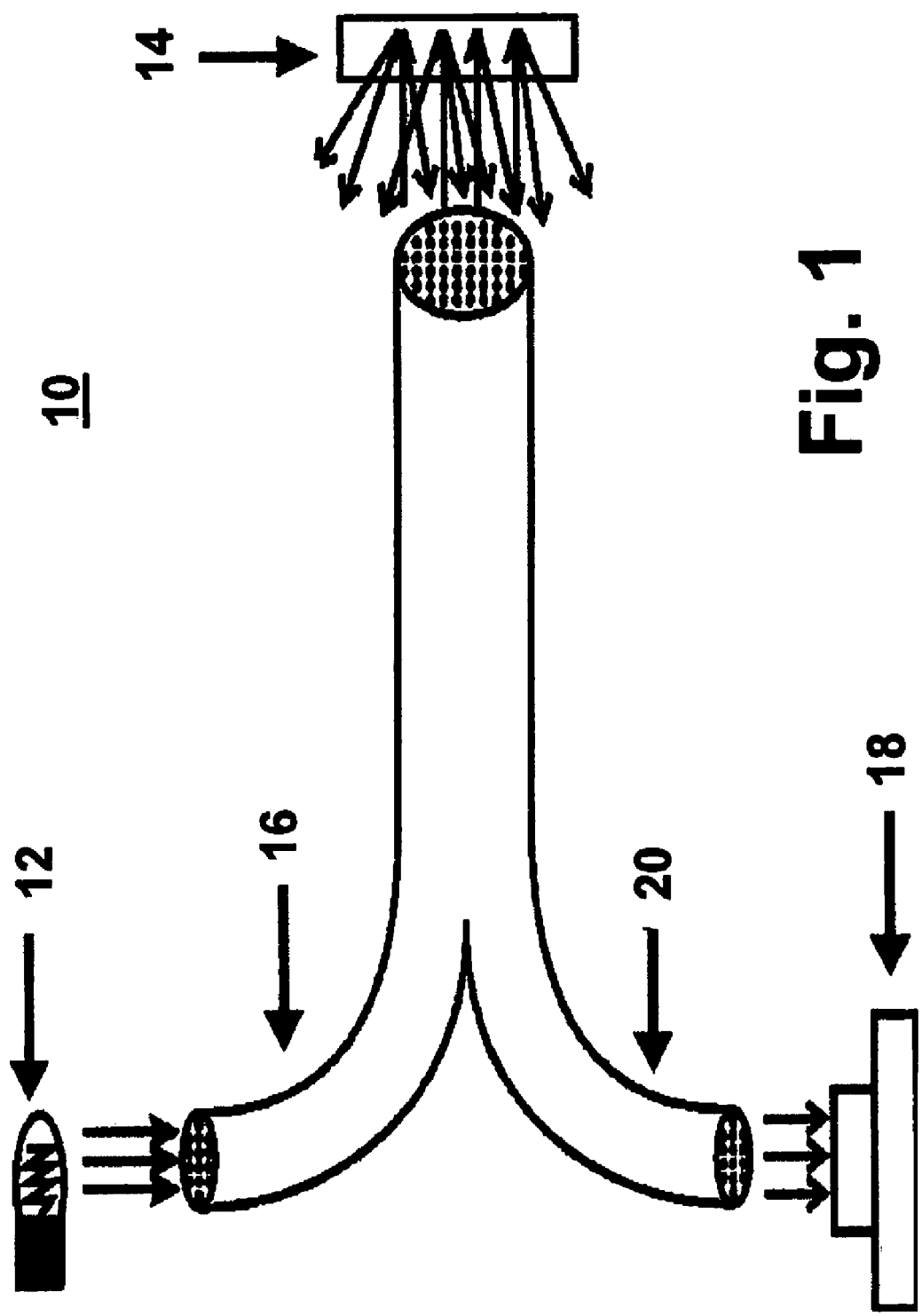
FIG. 1 is a representative drawing of a fibre optic probe of the type used in an FT-NIR device.

The novel features which are believed to be characteristic of the present invention, as to its structure, organization, use and method of operation, together with further objectives and advantages thereof, will be better understood from the following drawings in which a presently preferred embodiment of the invention will now be illustrated by way of example only. In the drawings, like reference numerals depict like elements.

It is expressly understood, however, that the drawings are for the purpose of illustration and description only and are not intended as a definition of the limits of the invention.

Scanning of different types of test material using the FT-NIR device involves exposing the test sample to NIR radiation. Some of the NIR radiation is absorbed by the sample, and the remaining NIR radiation is reflected, or transmitted through the sample. This reflected or transmitted NIR radiation is detected by a detector, and then analyzed.

In FIG. 1, a probe arrangement for the collection of reflected NIR radiation in and FT-NIR device is represented. As illustrated in FIG. 1, the Infrared source(12) emits a laser light beam of Near Infrared Radiation(NIR), which is delivered to the test sample(14) via a delivery fibre optic bundle (16). The NIR penetrates the sample(14) and specific wavelengths are absorbed or reflected. The reflected wavelengths are transmitted to a detector(18) via a collection fibre optic bundle(20). The reflected NIR wavelengths are recorded as an interferogram. The interferogram is then converted into a spectral reading, integrated, and the resulting data is collected and/or displayed as numerical values at selected wavelengths, or as spectral charts showing a range of wavelength absorption values.

A similar device might also be used to collect transmission radiation by having the Infrared source direct its radiation output directly at the detector with a gap between the source and the detector in which the test sample material is located.

FIGS. 2 to 5 show absorption or second derivative spectrum for a variety of materials as set out hereinbelow.

| FIG. No. | Material(s) and comments |
|---|---|
| 2 | Trielaidin and Triolein Absorption Spectrum |
| 3 | Second Derivative Spectrum comparison of Triolein and Trielaiden |

| FIG. No. | Material(s) and comments |
|---|---|
| 4 | Second Derivative Spectrum comparison of Triolein, Trilinolein and Trilinolenin |
| 5 | Second Derivative Spectrum comparison of Partially Hydrogenated Soy Oils having different Trans Fat levels |

In FIG. 2, the FT-NIR absorption spectrum for two similar fatty acids is shown. Triolein and Treilaidin have similar chemical compositions and molecular. weights, but differ in that Triolein contains a cis fatty acid and Treilaidin contains a trans fatty acid. The absorption spectra are similar but have minor differences.

In FIG. 3, a second derivative comparison of the absorption spectra from FIG. 2 is shown and the differences between the spectra of the two materials is shown with greater clarity.

FIG. 4 shows a similar second derivative comparison of Triolein with two other fats, namely Trilinolein and Trilinolenin. Again although the materials are similar in nature but have different chemical structures, the spectral differences between these materials is clearly evident.

In FIG. 5, a number of partially hydrogenated soy oils are compared having a trans fatty acid levels from between <1% (pure soy oil) to 100% (pure Trielaidin). Again, the spectral differences between the materials is evident.

Using the data from the spectral analysis shown in FIG. 5, mathematical factorized analysis can be conducted, and the results of comparative vector analysis can be plotted. In FIG. 6, a plot of two different vectors for the materials plotted in FIG. 5 is shown. Again, the plot shows the differences between the tested materials.

FIG. 7 shows a similar chart wherein additional material have been included. These additional materials include 9-cis 18:1; 9,12-cis 18:2; 9,12,15 cis 18:3; and 9-trans 18:1, which are representative of the pure fatty acids which might be found in a number of fats and oils. It can be seen that the pure soy oil lies between the three "cis" values, showing an approximation of the soy oil composition, and that increasing "trans" values show a progressive movement towards the 9-trans 18:1 value.

Also, our research has shown that the intensity of the absorption bands decreases as temperature at which oils/fats are tested increases. This temperature dependency has significant effect both on the identification and quantification models. In order to eliminate and/or minimize this temperature dependency and enhance the repeatability and reproducibility of the test method careful consideration is preferably given to temperature as a variable during the development stage of identification and quantification models. The models developed with temperature variable typically have a lower probability of producing erroneous results as well as making the models less dependent on testing temperature. The alternative would be to specify the temperature at which all oils/fats are scanned and strictly scan future test samples at pre-determined temperatures. However, the preferred approach is to address the temperature variability in the development stage to allow future test samples to be scanned at a range of practical temperatures. As such, preferably, the method of the present invention provides a method wherein the FT-NIR analysis is conducted at different temperatures, and the calibration matrix is modified to address the temperature variability encountered during analysis of the test sample material.

For example, FIG. 8 shows the identification of various oils/fats at different temperatures. Vector 2 represents the type of oil/fat and Vector 3 represents the testing temperature. As can be seen the type of material, as shown by Vector 2, is constant whereas the scanning temperature shows increase or decrease with change in temperature. Proper selection of the calibration matrix will account for the variations caused by the change in temperature.

Next, using the samples from FIG. 5, and additional samples having approximately 19 and 44% trans fatty acids, the samples were again tested and analyzed by FT-NIR, using the calibration matrix developed for this mixture. These values were compared to the results obtained by GC, and the results are presented in Tables 1A and 1B. It can clearly be seen that the results from the FT-NIR closely follow the results from the GC technique.

It should be noted that since the method of the present invention allows each fatty acid species to be separately identified and quantified, it is a simple matter to classify and total the amounts of fatty acids present in a sample, or alternatively, the desired total could be made as part of the mathematical model. As such, in Tables 1A and 1B, summary amounts are shown for Total Saturated Fat (T SAT), Total Cis Monounsaturated Fatty Acid (T C MUFA), Total Cis Polyunsaturated Fatty Acid (T C PUFA), Total trans Monounstaturated Fatty Acid (T MUFA trans), Total trans Double Unsaturated Fatty Acid (T DUFA trans), Total trans Triple Unstaturated Fatty Acid (T TUFA trans), and the Total Trans Fatty Acid (T Trans). Comparison of the values from the GC analysis and the FT-NIR analysis show a good correlation even when using the summation data. This is in spite of the fact that the FT-NIR spectra was taken over a matter of minutes, while the GC analysis took several hours for each sample.

In Table 2, the summation data for the <1%, 19%, 27%, 44% and 50% materials from Tables 1A and 1B are presented in a different format, for both the GC-HPLC and FT-NIR techniques.

In Table 3, a comparison of the results obtained on several oil samples using a suitable calibration matrix for FT-NIR was compared to the analysis obtained using GC-HPLC (Gas chromatography - high performance liquid chromatography). The results were obtained for the individual fatty acid components of soy oil, olive oil and flax oil samples.

It is to be noted that the amounts determined by the FT-NIR technique are in all cases similar to the amounts determined from the GC-HPLC technique. Further, it should be noted that again, the summation values at the bottom of Table 3 for Total Saturated Fat (T SAT), Total Cis Monounsaturated Fatty Acid (T C MUFA), Total Cis Polyunsaturated Fatty Acid (T C PUFA), Total trans Monounstaturated Fatty Acid (T MUFA trans), Total trans Double Unsaturated Fatty Acid (T DUFA trans), Total trans Triple Unstaturated Fatty Acid (T TUFA trans), and the Total Trans Fatty Acid (T Trans), are in agreement with the same values determined by the GC-HPLC technique even though the FT-NIR results were obtained in significantly less time.

Similarly, in Table 4, a comparison of the data obtained for representative samples of commercial Shortening and Lard materials is shown. The individual fatty acid components are listed, together with the total amounts described with respect to Table 3. Again, the FT-NIR technique provided individual fatty acid results, and total amounts similar to the GC-HPLC method for both shortening and lard.

The higher level of total trans fatty acid in the shortening sample should be noted.

In Table 5, the results of a further comparison between the results obtained from the GC-HPLC technique and the FT-NIR technique are shown. In this case, the data relate to the fatty acid components of the extracted fat from hydrogenated and non-hydrogenated margarine. Again, the individual fatty acid components are listed, together with the total amounts described with respect to Table 3. The FT-NIR technique again provided individual fatty acid results, and total amounts similar to the GC-HPLC method for both the extracted fat from hydrogenated and non-hydrogenated margarine.

The high level of total trans fat found in the hydrogenated sample should also be noted, when compared to the non-hydrogenated sample.

In Table 6, the results of a further analysis of margarine is provided which is similar to the results described in Table 5. However, in this case, the fat was not extracted from the margarine samples, and as such, the margarine samples were analyzed without any processing. For these samples, a significant water value was present (11 or 13%), and the weight percentage values shown are based on the total weight of the sample (including water). However, it is to be noted that this water level did not affect the accuracy of the results obtained by the FT-NIR procedure when compared to the GC technique.

In Table 7, a further comparison of two samples is shown. In this case, blends of shortening and lard are compared. The first sample contains 80% shortening and 20% lard. The second sample contains 21% shortening and 79% lard. Again the values for individual fatty acids as obtained from GC-HPLC and FT-NIR are listed, and there is a good agreement between the two techniques. Similarly, the summation values shown are also in good agreement.

The current FT-NIR method developed for oils/fats is also capable of identification and quantification of fatty acids within the triglyceride molecules in fish oil. However, due to the high concentrations of Omega-3 (LC) PUFAs in fish oil more specific identification and quantification models were developed with enhanced accuracy. Table 8 shows the fatty acid analysis for fish oils that were extracted from herring. Again the values for individual fatty acids as obtained from GC and FT-NIR are listed, and there is a good agreement between the two techniques. Similarly, the summation values shown are also in good agreement.

In view of these results, it has clearly been demonstrated that the use of FT-NIR, using a calibration matrix prepared from baseline sample testing using FT-NIR and a fatty acid reference analytical technique, which technique is preferably a GC technique, allows for subsequent rapid analysis of fatty acid-containing fats and/or oils with a high degree of specificity and accuracy. As a result, the use of FT-NIR for the analysis of a test sample provides a rapid, convenient method for the determination of the fatty acid content of a material. In particular, the FT-NIR technique described herein with respect to the present invention provides a rapid method for the determination of the trans fatty acid content, or the level of beneficial materials such as for example, Omega-3(LC) PUFA's, of a particular sample material.

Thus, it is apparent that there has been provided, in accordance with the present invention, a method for the analysis of fatty acid content in materials containing fats and/or oils, which fully satisfies the goals, objects, and advantages set forth hereinbefore. Therefore, having described specific embodiments of the present invention, it will be understood that alternatives, modifications and variations thereof may be suggested to those skilled in the art, and that it is intended that the present specification embrace all such alternatives, modifications and variations as fall within the scope of the appended claims.

Additionally, for clarity and unless otherwise stated, the word "comprise" and variations of the word such as "comprising" and "comprises", when used in the description and claims of the present specification, is not intended to exclude other additives, components, integers or steps.

Moreover, the words "substantially" or "essentially", when used with an adjective or adverb is intended to enhance the scope of the particular characteristic; e.g., substantially planar is intended to mean planar, nearly planar and/or exhibiting characteristics associated with a planar element.

Further, use of the terms "he", "him", or "his", is not intended to be specifically directed to persons of the masculine gender, and could easily be read as "she", "her", or "hers", respectively.

Also, while this discussion has addressed prior art known to the inventor, it is not an admission that all art discussed is citable against the present application.

TABLE 1A

Comparison of GC-HPLC and FT-NIR Results for Partially Hydrogenated Soy Oil

| No. | fatty acid | GC-HPLC % <1% Trans | FT-NIR % <1% Trans | GC-HPLC % 19% trans | FT-NIR % 19% trans | GC-HPLC % 27% trans | FT-NIR. % 27% trans |
|---|---|---|---|---|---|---|---|
| 1 | 10:0 | 0.02 | 0.02 | 0.02 | 0.02 | 0.03 | 0.03 |
| 2 | 12:0 | 0.04 | 0.05 | 0.03 | 0.06 | 0.03 | 0.04 |
| 3 | 14:0 | 0.09 | 0.10 | 0.08 | 0.05 | 0.08 | 0.08 |
| 4 | 16:0 | 10.44 | 10.56 | 9.98 | 9.75 | 9.62 | 9.90 |
| 5 | 9c-16:1 | 0.08 | 0.08 | 0.09 | 0.05 | 0.08 | 0.07 |
| 6 | 17:0 | 0.11 | 0.11 | 0.11 | 0.11 | 0.11 | 0.11 |
| 7 | 17:1 | 0.00 | 0.00 | 0.00 | 0.00 | 0.00 | 0.00 |
| 8 | 18:0 | 4.49 | 4.48 | 5.37 | 5.10 | 4.95 | 4.98 |
| 9 | 5t- | 0.00 | 0.00 | 0.03 | 0.03 | 0.10 | 0.10 |
| 10 | 6t-8t- | 0.04 | 0.01 | 1.23 | 1.25 | 2.13 | 2.11 |
| 11 | 9t- | 0.05 | 0.02 | 1.29 | 1.34 | 2.20 | 2.11 |
| 12 | 10t- | .0.08 | 0.07 | 3.89 | 3.84 | 4.87 | 4.90 |
| 13 | 11t- | 0.04 | 0.06 | 3.34 | 3.36 | 4.51 | 4.60 |
| 14 | 12t- | 0.02 | 0.01 | 1.37 | 1.40 | 2.19 | 2.20 |
| 15 | 13t/14t- | 0.04 | 0.04 | 1.89 | 1.88 | 2.85 | 2.86 |
| 16 | 9c- | 19.86 | 19.61 | 24.33 | 25.09 | 22.45 | 21.62 |
| 17 | 15t | 0.00 | −0.01 | 0.65 | 0.67 | 1.12 | 1.12 |
| 18 | 11c- | 1.40 | 1.40 | 1.95 | 2.05 | 2.24 | 2.17 |
| 19 | 12c- | 0.04 | 0.10 | 5.86 | 5.52 | 4.56 | 4.72 |
| 20 | 13c- | 0.05 | 0.05 | 0.30 | 0.30 | 0.45 | 0.45 |
| 21 | 14c/16t- | 0.00 | 0.00 | 0.21 | 0.20 | 0.39 | 0.39 |
| 22 | 14c | 0.00 | 0.00 | 0.17 | 0.16 | 0.21 | 0.21 |
| 23 | 19:0 | 0.01 | 0.01 | 0.53 | 0.49 | 0.48 | 0.48 |
| 24 | 9t12t-18:2 | 0.00 | 0.00 | 0.11 | 0.11 | 0.15 | 0.15 |
| 25 | 9c13t- | 0.02 | 0.05 | 1.52 | 1.45 | 1.88 | 1.89 |
| 26 | 9c 12t 18:2 | 0.06 | 0.09 | 1.34 | 1.25 | 1.68 | 1.65 |
| 27 | 9t, 12c 18:2 | 0.01 | 0.03 | 1.20 | 1.11 | 1.50 | 1.47 |
| 28 | 11t, 15c 18:2 | 0.00 | 0.00 | 0.49 | 0.46 | 0.51 | 0.51 |
| 29 | 18:2n6 | 52.70 | 52.78 | 26.57 | 26.69 | 21.52 | 21.70 |
| 30 | 20:0 | 0.36 | 0.35 | 0.37 | 0.39 | 0.36 | 0.36 |
| 31 | cct-18:3 | 0.04 | 0.05 | 0.19 | 0.21 | 0.19 | 0.17 |
| 32 | 9c-20:1, ctc | 0.02 | 0.02 | 0.04 | 0.05 | 0.05 | 0.05 |
| 33 | 10c-20:1, cct | 0.02 | 0.02 | 0.10 | 0.13 | 0.12 | 0.10 |
| 34 | 11c-20:1 | 0.17 | 0.16 | 0.18 | 0.22 | 0.16 | 0.12 |
| 35 | 18:3n3 | 8.85 | 8.83 | 2.03 | 1.84 | 1.43 | 1.27 |
| 36 | 9c11t-CLA | 0.04 | 0.07 | 0.07 | 0.07 | 0.23 | 0.23 |
| 37 | 20:2n6 | 0.04 | 0.04 | 0.02 | 0.01 | 0.02 | 0.02 |
| 38 | 22:0 | 0.36 | 0.36 | 0.37 | 0.36 | 0.38 | 0.37 |
| 39 | 24:0 | 0.10 | 0.10 | 0.10 | 0.10 | 0.10 | 0.10 |
| 40 | T Sat | 16.04 | 16.17 | 16.96 | 16.52 | 16.13 | 16.56 |
| 41 | T C MUFA | 21.52 | 21.32 | 32.79 | 33.22 | 30.08 | 29.25 |
| 42 | T C PUFA | 61.59 | 61.65 | 28.62 | 29.06 | 22.97 | 23.45 |
| 43 | T MUFA trans | 0.27 | 0.16 | 13.89 | 14.14 | 20.37 | 20.56 |
| 44 | T DUFA trans | 0.13 | 0.24 | 4.73 | 4.43 | 5.95 | 5.87 |
| 45 | T TUFA trans | 0.08 | 0.09 | 0.34 | 0.39 | 0.36 | 0.31 |
| 46 | T Trans | 0.47 | 0.47 | 18.96 | 18.80 | 26.69 | 26.71 |

GC-HPLC = Gas Chromatography High Performance Liquid Chromatography
FT-NIR = Fourier Transform Near Infrared Spectroscopy

TABLE 1B

Comparison of GC-HPLC and FT-NIR Results for Partially Hydrogenated Soy Oil

| No. | fatty acid | GC-HPLC % 44% trans | FT-NIR % 44% trans | GC-HPLC % 50% trans | FT-NIR % 50% trans |
|---|---|---|---|---|---|
| 1 | 10:0 | 0.02 | 0.02 | 0.02 | 0.02 |
| 2 | 12:0 | 0.04 | −0.01 | 0.02 | −0.07 |
| 3 | 14:0 | 0.08 | 0.05 | 0.08 | 0.08 |
| 4 | 16:0 | 9.94 | 9.78 | 10.00 | 10.41 |
| 5 | 9c-16:1 | 0.06 | 0.05 | 0.04 | 0.12 |
| 6 | 17:0 | 0.11 | 0.11 | 0.12 | 0.13 |
| 7 | 17:1 | 0.00 | 0.00 | 0.00 | 0.01 |
| 8 | 18:0 | 6.89 | 6.93 | 12.31 | 12.52 |
| 9 | 5t- | 0.14 | 0.14 | 0.27 | 0.26 |
| 10 | 6t-8t- | 4.08 | 4.13 | 6.47 | 6.31 |
| 11 | 9t- | 4.99 | 5.07 | 6.66 | 6.67 |
| 12 | 10t- | 9.39 | 9.36 | 10.01 | 9.98 |
| 13 | 11t- | 8.35 | 8.30 | 8.29 | 8.25 |
| 14 | 12t- | 4.59 | 4.56 | 5.66 | 5.55 |
| 15 | 13t/14t- | 5.13 | 5.12 | 6.90 | 6.75 |
| 16 | 9c- | 20.61 | 20.56 | 13.91 | 13.41 |
| 17 | 15t | 2.27 | 2.27 | 3.03 | 2.95 |
| 18 | 11c- | 2.84 | 2.83 | 2.81 | 2.79 |
| 19 | 12c- | 6.57 | 6.44 | 4.85 | 4.98 |
| 20 | 13c- | 0.76 | 0.76 | 1.03 | 1.01 |
| 21 | 14c/16t- | 0.53 | 0.54 | 0.75 | 0.75 |
| 22 | 14c | 0.42 | 0.42 | 0.55 | 0.54 |
| 23 | 19:0 | 0.69 | 0.69 | 0.68 | 0.69 |
| 24 | 9t12t-18:2 | 0.20 | 0.20 | 0.14 | 0.15 |
| 25 | 9c13t- | 1.96 | 1.95 | 1.11 | 1.20 |
| 26 | 9c 12t 18:2 | 0.73 | 0.73 | 0.41 | 0.48 |
| 27 | 9t, 12c 18:2 | 0.60 | 0.60 | 0.18 | 0.25 |
| 28 | 11t, 15c 18:2 | 0.54 | 0.53 | 0.36 | 0.38 |
| 29 | 18:2n6 | 3.41 | 4.07 | 0.35 | 0.73 |
| 30 | 20:0 | 0.37 | 0.39 | 0.38 | 0.36 |
| 31 | cct-18:3 | 0.02 | −0.03 | 0.00 | −0.03 |
| 32 | 9c-20:1, ctc | 0.02 | 0.02 | 0.02 | 0.01 |
| 33 | 10c-20:1, cct | 0.02 | −0.02 | 0.00 | −0.03 |
| 34 | 11c-20:1 | 0.12 | 0.13 | 0.08 | 0.08 |
| 35 | 18:3n3 | 0.16 | −0.11 | 0.00 | 0.18 |
| 36 | 9c11t-CLA | 0.06 | 0.06 | 0.01 | 0.01 |
| 37 | 20:2n6 | 0.00 | 0.00 | 0.00 | 0.02 |
| 38 | 22:0 | 0.36 | 0.36 | 0.36 | 0.36 |
| 39 | 24:0 | 0.10 | 0.11 | 0.10 | 0.10 |
| 40 | T Sat | 18.60 | 18.55 | 24.09 | 24.58 |
| 41 | T C MUFA | 31.33 | 31.23 | 23.22 | 22.84 |
| 42 | T C PUFA | 3.57 | 4.02 | 0.35 | 0.47 |
| 43 | T MUFA trans | 39.46 | 39.56 | 48.04 | 47.51 |
| 44 | T DUFA trans | 4.08 | 4.03 | 2.20 | 2.47 |
| 45 | T TUFA trans | 0.06 | −0.03 | 0.02 | −0.05 |
| 46 | T Trans | 43.60 | 43.49 | 50.25 | 49.85 |

GC-HPLC = Gas Chromatography High Performance Liquid Chromatography
FT-NIR = Fourier Transform Near Infrared Spectroscopy

TABLE 2

Summary of Total Fatty Acids for Partially Hydrogenated Soy Oils

| | | Summary Totals | | | | | | |
|---|---|---|---|---|---|---|---|---|
| | | T Sat | T C MUFA | T C PUFA | T MUFA trans | T DUFA trans | T TUFA trans | T Trans |
| GC-HPLC % | Soy Oil <1 trans | 16.04 | 21.52 | 61.59 | 0.27 | 0.13 | 0.08 | 0.47 |
| FT-NIR % | Soy Oil <1 trans | 16.17 | 21.32 | 61.65 | 0.16 | 0.24 | 0.09 | 0.47 |
| GC-HPLC % | Soy Oil 19% trans | 16.96 | 32.79 | 28.62 | 13.89 | 4.73 | 0.34 | 18.96 |
| FT-NIR % | Soy Oil 19% trans | 16.52 | 33.22 | 29.06 | 14.14 | 4.43 | 0.39 | 18.80 |
| GC-HPLC % | Soy Oil 27% trans | 16.13 | 30.08 | 22.97 | 20.37 | 5.95 | 0.36 | 26.69 |
| FT-NIR % | Soy Oil 27% trans | 16.56 | 29.25 | 23.45 | 20.56 | 5.87 | 0.31 | 26.71 |
| GC-HPLC % | Soy Oil 44% trans | 18.60 | 31.33 | 3.57 | 39.46 | 4.08 | 0.06 | 43.60 |
| FT-NIR % | Soy Oil 44% trans | 18.55 | 31.23 | 4.02 | 39.56 | 4.03 | −0.03 | 43.49 |
| GC-HPLC % | Soy Oil 50% trans | 24.09 | 23.22 | 0.35 | 48.04 | 2.20 | 0.02 | 50.25 |
| FT-NIR % | Soy Oil 50% trans | 24.58 | 22.84 | 0.47 | 47.51 | 2.47 | −0.05 | 49.85 |

GC-HPLC = Gas Chromatography High Performance Liquid Chromatography
FT-NIR = Fourier Transform Near Infrared Spectroscopy

TABLE 3

Comparison of GC-HPLC and FT-NIR Results for Different Oils

| No. | fatty acid | GC-HPLC % Soy Oil | FT-NIR % Soy Oil | GC-HPLC % Olive Oil | FT-NIR % Olive Oil | GC-HPLC % Flax Oil | FT-NIR % Flax Oil |
|---|---|---|---|---|---|---|---|
| 1 | 10:0 | 0.02 | 0.02 | 0.02 | 0.02 | 0.02 | 0.02 |
| 2 | 12:0 | 0.04 | 0.05 | 0.04 | 0.06 | 0.04 | 0.04 |
| 3 | 14:0 | 0.09 | 0.10 | 0.41 | 0.42 | 0.43 | 0.42 |
| 4 | 16:0 | 10.44 | 10.56 | 11.49 | 11.50 | 4.93 | 4.78 |
| 5 | 9c-16:1 | 0.08 | 0.08 | 0.75 | 0.75 | 0.05 | 0.05 |
| 6 | 17:0 | 0.11 | 0.11 | 0.06 | 0.06 | 0.06 | 0.06 |
| 7 | 17:1 | 0.00 | 0.00 | 0.09 | 0.09 | 0.04 | 0.04 |
| 8 | 18:0 | 4.49 | 4.48 | 2.76 | 2.77 | 4.31 | 4.26 |
| 9 | 5t- | 0.00 | 0.00 | 0.00 | 0.00 | 0.00 | 0.00 |
| 10 | 6t-8t- | 0.04 | 0.01 | 0.05 | 0.03 | 0.01 | 0.02 |
| 11 | 9t- | 0.05 | 0.02 | 0.15 | 0.16 | 0.01 | 0.07 |

TABLE 3-continued

Comparison of GC-HPLC and FT-NIR Results for Different Oils

| No. | fatty acid | GC-HPLC % Soy Oil | FT-NIR % Soy Oil | GC-HPLC % Olive Oil | FT-NIR % Olive Oil | GC-HPLC % Flax Oil | FT-NIR % Flax Oil |
|---|---|---|---|---|---|---|---|
| 12 | 10t- | 0.08 | 0.07 | 0.06 | 0.03 | 0.02 | 0.03 |
| 13 | 11t- | 0.04 | 0.06 | 0.01 | −0.02 | 0.01 | 0.01 |
| 14 | 12t- | 0.02 | 0.01 | 0.01 | −0.01 | 0.01 | 0.02 |
| 15 | 13t/14t- | 0.04 | 0.04 | 0.01 | −0.02 | 0.00 | 0.01 |
| 16 | 9c- | 19.86 | 19.61 | 68.34 | 68.55 | 20.20 | 20.04 |
| 17 | 15t | 0.00 | −0.01 | 0.00 | −0.01 | 0.00 | 0.01 |
| 18 | 11c- | 1.40 | 1.40 | 2.05 | 2.07 | 0.66 | 0.64 |
| 19 | 12c- | 0.04 | 0.10 | 0.00 | −0.02 | 0.01 | −0.01 |
| 20 | 13c- | 0.05 | 0.05 | 0.00 | 0.00 | 0.01 | 0.01 |
| 21 | 14c/16t- | 0.00 | 0.00 | 0.00 | 0.00 | 0.00 | 0.00 |
| 22 | 14c | 0.00 | 0.00 | 0.00 | 0.00 | 0.00 | 0.00 |
| 23 | 19:0 | 0.01 | 0.01 | 0.00 | 0.00 | 0.00 | 0.00 |
| 24 | 9t12t-18:2 | 0.00 | 0.00 | 0.00 | 0.00 | 0.00 | 0.00 |
| 25 | 9c13t- | 0.02 | 0.05 | 0.00 | 0.00 | 0.00 | 0.00 |
| 26 | 9c 12t 18:2 | 0.06 | 0.09 | 0.06 | 0.06 | 0.06 | 0.06 |
| 27 | 9t, 12c 18:2 | 0.01 | 0.03 | 0.04 | 0.04 | 0.01 | 0.01 |
| 28 | 11t, 15c 18:2 | 0.00 | 0.00 | 0.00 | 0.00 | 0.00 | 0.00 |
| 29 | 18:2n6 | 52.70 | 52.78 | 10.68 | 10.55 | 15.40 | 15.68 |
| 30 | 20:0 | 0.36 | 0.35 | 0.52 | 0.52 | 0.17 | 0.16 |
| 31 | cct-18:3 | 0.04 | 0.05 | 0.03 | 0.04 | 0.23 | 0.21 |
| 32 | 9c-20:1, ctc | 0.02 | 0.02 | 0.02 | 0.02 | 0.02 | 0.02 |
| 33 | 10c-20:1, cct | 0.02 | 0.02 | 0.03 | 0.04 | 0.04 | 0.03 |
| 34 | 11c-20:1 | 0.17 | 0.16 | 0.36 | 0.37 | 0.18 | 0.18 |
| 35 | 18:3n3 | 8.85 | 8.83 | 0.64 | 0.68 | 51.83 | 51.88 |
| 36 | 9c11t-CLA | 0.04 | 0.07 | 0.06 | 0.06 | 0.02 | 0.02 |
| 37 | 20:2n6 | 0.04 | 0.04 | 0.00 | 0.00 | 0.04 | 0.04 |
| 38 | 22:0 | 0.36 | 0.36 | 0.24 | 0.24 | 0.14 | 0.14 |
| 39 | 24:0 | 0.10 | 0.10 | 0.10 | 0.10 | 0.09 | 0.09 |
| 40 | T Sat | 16.04 | 16.17 | 15.64 | 15.67 | 10.20 | 9.96 |
| 41 | T C MUFA | 21.52 | 21.32 | 70.84 | 70.99 | 21.11 | 20.92 |
| 42 | T C PUFA | 61.59 | 61.65 | 11.32 | 11.31 | 67.27 | 67.60 |
| 43 | T MUFA trans | 0.27 | 0.16 | 0.30 | 0.14 | 0.05 | 0.14 |
| 44 | T DUFA trans | 0.13 | 0.24 | 0.16 | 0.16 | 0.09 | 0.09 |
| 45 | T TUFA trans | 0.08 | 0.09 | 0.07 | 0.09 | 0.29 | 0.26 |
| 46 | T Trans | 0.47 | 0.47 | 0.52 | 0.39 | 0.44 | 0.51 |

GC-HPLC = Gas Chromatography High Performance Liquid Chromatography
FT-NIR = Fourier Transform Near Infrared Spectroscopy

TABLE 4

Comparison of GC-HPLC and FT-NIR Results for Shortening and Lard

| No. | fatty acid | GC-HPLC % Shortening | FT-NIR % Shortening | GC-HPLC % Lard | FT-NIR % Lard |
|---|---|---|---|---|---|
| 1 | 10:0 | 0.07 | 0.07 | 0.05 | 0.05 |
| 2 | 12:0 | 0.03 | 0.04 | 0.06 | 0.02 |
| 3 | 14:0 | 0.21 | 0.21 | 1.30 | 1.29 |
| 4 | 16:0 | 16.01 | 16.17 | 24.21 | 24.22 |
| 5 | 9c-16:1 | 0.10 | 0.10 | 1.88 | 1.89 |
| 6 | 17:0 | 0.11 | 0.11 | 0.38 | 0.38 |
| 7 | 17:1 | 0.06 | 0.06 | 0.27 | 0.27 |
| 8 | 18:0 | 11.04 | 11.03 | 14.64 | 14.75 |
| 9 | 5t- | 0.06 | 0.06 | 0.03 | 0.03 |
| 10 | 6t-8t- | 1.60 | 1.58 | 0.36 | 0.37 |
| 11 | 9t- | 2.11 | 2.05 | 0.66 | 0.66 |
| 12 | 10t- | 4.08 | 4.11 | 0.55 | 0.54 |
| 13 | 11t- | 3.79 | 3.83 | 0.35 | 0.35 |
| 14 | 12t- | 1.43 | 1.43 | 0.17 | 0.18 |
| 15 | 13t/14t- | 1.86 | 1.87 | 0.24 | 0.25 |
| 16 | 9c- | 24.46 | 24.05 | 36.36 | 36.37 |
| 17 | 15t | 0.65 | 0.65 | 0.00 | 0.00 |
| 18 | 11c- | 1.69 | 1.68 | 2.44 | 2.44 |
| 19 | 12c- | 4.11 | 4.22 | 0.17 | 0.10 |
| 20 | 13c- | 0.23 | 0.23 | 0.13 | 0.13 |
| 21 | 14c/16t- | 0.14 | 0.14 | 0.03 | 0.03 |
| 22 | 14c | 0.14 | 0.14 | 0.03 | 0.03 |
| 23 | 19:0 | 0.00 | 0.01 | 0.03 | 0.02 |
| 24 | 9t12t-18:2 | 0.11 | 0.11 | 0.01 | 0.01 |
| 25 | 9c13t- | 0.92 | 0.96 | 0.10 | 0.07 |
| 26 | 9c 12t 18:2 | 1.33 | 1.36 | 0.21 | 0.18 |
| 27 | 9t, 12c 18:2 | 1.05 | 1.08 | 0.15 | 0.12 |
| 28 | 11t, 15c 18:2 | 0.22 | 0.23 | 0.00 | −0.01 |
| 29 | 18:2n6 | 19.68 | 19.76 | 12.41 | 12.54 |
| 30 | 20:0 | 0.40 | 0.39 | 0.25 | 0.25 |
| 31 | cct-18:3 | 0.23 | 0.24 | 0.09 | 0.08 |
| 32 | 9c-20:1, ctc | 0.16 | 0.16 | 0.00 | 0.00 |
| 33 | 10c-20:1, cct | 0.20 | 0.20 | 0.05 | 0.04 |
| 34 | 11c-20:1 | 0.20 | 0.19 | 0.62 | 0.62 |
| 35 | 18:3n3 | 0.97 | 0.95 | 0.55 | 0.56 |
| 36 | 9c11t-CLA | 0.17 | 0.18 | 0.06 | 0.05 |
| 37 | 20:2n6 | 0.00 | 0.00 | 0.46 | 0.46 |
| 38 | 22:0 | 0.31 | 0.31 | 0.03 | 0.03 |
| 39 | 24:0 | 0.10 | 0.10 | 0.02 | 0.02 |

TABLE 4-continued

Comparison of GC-HPLC and FT-NIR Results for Shortening and Lard

| No. | fatty acid | GC-HPLC % Shortening | FT-NIR % Shortening | GC-HPLC % Lard | FT-NIR % Lard |
|---|---|---|---|---|---|
| 40 | T Sat | 28.27 | 28.42 | 40.97 | 41.03 |
| 41 | T C MUFA | 30.90 | 30.55 | 40.01 | 39.94 |
| 42 | T C PUFA | 20.65 | 20.70 | 13.41 | 13.56 |
| 43 | T MUFA trans | 15.71 | 15.69 | 2.39 | 2.42 |
| 44 | T DUFA trans | 3.79 | 3.91 | 0.53 | 0.42 |
| 45 | T TUFA trans | 0.58 | 0.59 | 0.14 | 0.12 |
| 46 | T Trans | 20.09 | 20.20 | 3.06 | 2.96 |

GC-HPLC = Gas Chromatography High Performance Liquid Chromatography
FT-NIR = Fourier Transform Near Infrared Spectroscopy

TABLE 5

Comparison of GC-HPLC and FT-NIR Results for Extracted Fat from Margarine

| No. | fatty acid | GC-HPLC % Hydrogenated | FT-NIR % Hydrogenated | GC-HPLC % Non-Hydrogenated | FT-NIR % Non-Hydrogenated |
|---|---|---|---|---|---|
| 1 | 10:0 | 0.01 | 0.01 | 0.05 | 0.05 |
| 2 | 12:0 | 0.02 | 0.02 | 1.91 | 1.92 |
| 3 | 14:0 | 0.06 | 0.07 | 1.06 | 1.06 |
| 4 | 16:0 | 4.57 | 4.70 | 11.27 | 11.26 |
| 5 | 9c-16:1 | 0.15 | 0.15 | 0.19 | 0.19 |
| 6 | 17:0 | 0.07 | 0.07 | 0.07 | 0.07 |
| 7 | 17:1 | 0.05 | 0.05 | 0.07 | 0.07 |
| 8 | 18:0 | 7.18 | 7.13 | 2.87 | 2.87 |
| 9 | 5t- | 0.08 | 0.08 | 0.00 | 0.00 |
| 10 | 6t-8t- | 3.88 | 3.82 | 0.07 | 0.07 |
| 11 | 9t- | 7.87 | 7.74 | 0.14 | 0.13 |
| 12 | 10t- | 5.36 | 5.37 | 0.13 | 0.13 |
| 13 | 11t- | 3.04 | 3.10 | 0.05 | 0.02 |
| 14 | 12t- | 1.98 | 1.99 | 0.04 | 0.03 |
| 15 | 13t/14t- | 2.47 | 2.48 | 0.05 | 0.05 |
| 16 | 9c- | 42.42 | 42.54 | 51.70 | 51.73 |
| 17 | 15t | 1.38 | 1.37 | 0.00 | 0.00 |
| 18 | 11c- | 2.89 | 2.90 | 2.82 | 2.81 |
| 19 | 12c- | 2.19 | 2.35 | 0.03 | 0.07 |
| 20 | 13c- | 0.28 | 0.28 | 0.03 | 0.03 |
| 21 | 14c/16t- | 0.40 | 0.40 | 0.01 | 0.01 |
| 22 | 14c | 0.20 | 0.20 | 0.00 | 0.00 |
| 23 | 19:0 | 0.43 | 0.44 | 0.01 | 0.01 |
| 24 | 9t12t-18:2 | 0.41 | 0.40 | 0.02 | 0.02 |
| 25 | 9c13t- | 1.08 | 1.09 | 0.03 | 0.03 |
| 26 | 9c 12t 18:2 | 1.04 | 1.02 | 0.16 | 0.16 |
| 27 | 9t, 12c 18:2 | 0.95 | 0.95 | 0.14 | 0.15 |
| 28 | 11t, 15c 18:2 | 0.48 | 0.47 | 0.00 | 0.00 |
| 29 | 18:2n6 | 3.43 | 3.24 | 16.59 | 16.65 |
| 30 | 20:0 | 0.73 | 0.73 | 0.59 | 0.59 |
| 31 | cct-18:3 | 0.15 | 0.16 | 0.67 | 0.66 |
| 32 | 9c-20:1, ctc | 0.09 | 0.09 | 0.11 | 0.11 |
| 33 | 10c-20:1, cct | 0.12 | 0.12 | 0.59 | 0.59 |
| 34 | 11c-20:1 | 0.83 | 0.83 | 1.12 | 1.12 |
| 35 | 18:3n3 | 0.56 | 0.59 | 6.24 | 6.17 |
| 36 | 9c11t-CLA | 0.19 | 0.18 | 0.06 | 0.04 |
| 37 | 20:2n6 | 0.02 | 0.02 | 0.06 | 0.06 |
| 38 | 22:0 | 0.29 | 0.29 | 0.28 | 0.28 |
| 39 | 24:0 | 0.11 | 0.11 | 0.10 | 0.10 |
| 40 | T Sat | 13.49 | 13.51 | 18.23 | 18.25 |
| 41 | T C MUFA | 48.87 | 49.07 | 55.77 | 55.82 |
| 42 | T C PUFA | 4.00 | 3.93 | 22.88 | 22.87 |
| 43 | T MUFA trans | 26.45 | 26.34 | 0.49 | 0.46 |
| 44 | T DUFA trans | 4.15 | 4.12 | 0.41 | 0.42 |
| 45 | T TUFA trans | 0.36 | 0.36 | 1.37 | 1.36 |
| 46 | T Trans | 30.95 | 30.82 | 2.26 | 2.21 |

GC-HPLC = Gas Chromatography High Performance Liquid Chromatography
FT-NIR = Fourier Transform Near Infrared Spectroscopy

TABLE 6

Comparison of GC-HPLC and FT-NIR (Direct Measurement) Results for Hydrogenated and Non-Hydrogenated Margarine

| No. | fatty acid | GC-HPLC Hydrog. Margarine | FT-NIR Hydrog. Margarine | GC-HPLC Non-Hydrog. Margarine | FT-NIR Non-Hydrog. Margarine |
|---|---|---|---|---|---|
| 1 | 10:0 | 0.01 | 0.01 | 0.04 | 0.04 |
| 2 | 12:0 | 0.02 | −0.05 | 1.66 | 1.60 |
| 3 | 14:0 | 0.05 | 0.02 | 0.93 | 0.90 |
| 4 | 16:0 | 4.07 | 3.92 | 9.80 | 9.70 |
| 5 | 9c, 16:1 | 0.13 | 0.13 | 0.16 | 0.16 |
| 6 | 17:0 | 0.07 | 0.07 | 0.07 | 0.07 |
| 7 | 9c-17:1 | 0.01 | 0.01 | 0.06 | 0.06 |
| 8 | 11c-17:1 | 0.05 | 0.05 | 0.06 | 0.06 |
| 9 | 18:0 | 6.39 | 6.35 | 2.50 | 2.55 |
| 10 | 5t | 0.07 | 0.07 | 0.00 | 0.00 |
| 11 | 6-8t | 3.45 | 3.48 | 0.06 | 0.11 |
| 12 | 9t | 7.00 | 7.04 | 0.13 | 0.19 |
| 13 | 10t | 4.77 | 4.84 | 0.11 | 0.15 |
| 14 | 11t | 2.70 | 2.75 | 0.04 | 0.07 |
| 15 | 12t | 1.76 | 1.82 | 0.03 | 0.03 |
| 16 | 13t, 14t | 2.20 | 2.23 | 0.04 | 0.09 |
| 17 | 9c-18:1 | 37.76 | 37.30 | 44.98 | 44.42 |
| 18 | 15t | 1.22 | 1.24 | 0.00 | 0.01 |
| 19 | 11c-18:1 | 2.57 | 2.55 | 2.45 | 2.41 |
| 20 | 12c | 1.95 | 1.93 | 0.03 | 0.05 |
| 21 | 13c | 0.25 | 0.26 | 0.02 | 0.02 |
| 22 | 14c/16t | 0.36 | 0.37 | 0.01 | 0.01 |
| 23 | 19:0/15c | 0.38 | 0.39 | 0.01 | 0.01 |
| 24 | 9t12t-18:2 | 0.37 | 0.37 | 0.02 | 0.02 |
| 25 | 9c13t-18:2 | 0.97 | 0.96 | 0.03 | 0.04 |
| 26 | 8, 12-18:2 | 0.22 | 0.22 | 0.00 | 0.00 |
| 27 | 9c12t-18:2 | 0.92 | 0.91 | 0.14 | 0.15 |
| 28 | 9t12c-18:2 | 0.85 | 0.84 | 0.12 | 0.12 |
| 29 | 11t15c-18:2 | 0.42 | 0.42 | 0.00 | 0.00 |
| 30 | 18:2n6 | 3.05 | 3.39 | 14.43 | 15.13 |
| 31 | 9c15c-18:2 | 0.06 | 0.06 | 0.03 | 0.03 |
| 32 | c, c-18:2 | 0.46 | 0.45 | 0.02 | 0.02 |
| 33 | 20:0 | 0.65 | 0.64 | 0.52 | 0.52 |
| 34 | 18:3n-6 | 0.09 | 0.09 | 0.04 | 0.04 |
| 35 | 18:3 cct- | 0.13 | 0.12 | 0.58 | 0.56 |
| 36 | 18:3 ctc | 0.08 | 0.08 | 0.10 | 0.10 |
| 37 | 18:3 tcc | 0.11 | 0.10 | 0.51 | 0.49 |
| 38 | 20:1-11c | 0.74 | 0.72 | 0.97 | 0.94 |
| 39 | 18:3n3 | 0.50 | 0.46 | 5.43 | 5.34 |
| 40 | 9t11t/10t12t | 0.17 | 0.17 | 0.05 | 0.05 |
| 41 | 20:2n6 | 0.01 | 0.01 | 0.05 | 0.05 |
| 42 | 22:0 | 0.26 | 0.26 | 0.25 | 0.25 |
| 43 | 24:0 | 0.10 | 0.10 | 0.09 | 0.09 |
| 44 | TSat | 12.01 | 11.67 | 15.86 | 15.78 |
| 45 | T MUFA cis | 43.46 | 42.96 | 48.74 | 48.17 |
| 46 | T PUFA cis | 3.65 | 3.94 | 19.95 | 20.51 |
| 47 | T MUFA tr | 23.54 | 23.90 | 0.43 | 0.62 |
| 48 | T DUFA tr | 3.75 | 3.72 | 0.31 | 0.34 |
| 49 | T TUFA tr | 0.32 | 0.29 | 1.19 | 1.15 |
| 50 | T trans | 27.60 | 27.86 | 1.92 | 2.11 |
| 51 | Water % | 11.00 | 11.22 | 13.00 | 13.20 |

GC-HPLC = Gas Chromatography High Performance Liquid Chromatography
FT-NIR = Fourier Transform Near Infrared Spectroscopy

TABLE 7

Validation of FT-NIR Method for Mixtures of Shortening and Lard

| No. | fatty acid | GC-HPLC % 80% Short. 20% Lard | FT-NIR % 80% Short. 20% Lard | GC-HPLC % 21% Short. 79% Lard | FT-NIR % 21% Short. 79% Lard |
|---|---|---|---|---|---|
| 1 | 10:0 | 0.06 | 0.06 | 0.06 | 0.05 |
| 2 | 12:0 | 0.04 | 0.03 | 0.04 | 0.07 |
| 3 | 14:0 | 0.23 | 0.44 | 0.32 | 1.12 |
| 4 | 16:0 | 17.01 | 17.22 | 22.03 | 23.49 |
| 5 | 9c-16:1 | 0.45 | 0.54 | 1.57 | 1.56 |
| 6 | 17:0 | 0.18 | 0.15 | 0.35 | 0.32 |
| 7 | 17:1 | 0.10 | 0.09 | 0.25 | 0.22 |
| 8 | 18:0 | 10.63 | 10.69 | 13.09 | 13.90 |
| 9 | 5t- | 0.03 | 0.07 | 0.00 | 0.05 |

TABLE 7-continued

Validation of FT-NIR Method for Mixtures of Shortening and Lard

| No. | fatty acid | GC-HPLC % 80% Short. 20% Lard | FT-NIR % 80% Short. 20% Lard | GC-HPLC % 21% Short. 79% Lard | FT-NIR % 21% Short. 79% Lard |
|---|---|---|---|---|---|
| 10 | 6t-8t- | 1.32 | 1.51 | 0.47 | 0.81 |
| 11 | 9t- | 1.56 | 1.77 | 0.62 | 1.27 |
| 12 | 10t- | 3.35 | 3.31 | 1.08 | 1.34 |
| 13 | 11t- | 2.50 | 3.07 | 0.82 | 1.04 |
| 14 | 12t- | 1.12 | 1.37 | 0.38 | 0.58 |
| 15 | 13t/14t- | 1.11 | 1.72 | 0.45 | 0.72 |
| 16 | 9c- | 27.10 | 28.83 | 34.53 | 35.17 |
| 17 | 15t | 0.30 | 0.62 | 0.20 | 0.24 |
| 18 | 11c- | 1.85 | 1.58 | 2.38 | 1.97 |
| 19 | 12c- | 3.40 | 2.81 | 1.04 | 0.54 |
| 20 | 13c- | 0.22 | 0.24 | 0.15 | 0.17 |
| 21 | 14C/16C- | 0.11 | 0.16 | 0.05 | 0.07 |
| 22 | 14c | 0.11 | 0.14 | 0.05 | 0.06 |
| 23 | 19:0 | 0.28 | 0.04 | 0.14 | 0.02 |
| 24 | 9t12t-18:2 | 0.10 | 0.07 | 0.03 | 0.03 |
| 25 | 9c13t- | 0.77 | 0.61 | 0.25 | 0.16 |
| 26 | 9c 12t 18:2 | 1.26 | 0.83 | 0.50 | 0.28 |
| 27 | 9t, 12c 18:2 | 1.04 | 0.62 | 0.41 | 0.18 |
| 28 | 11t, 15c 18:2 | 0.26 | 0.14 | 0.06 | 0.01 |
| 29 | 18:2n6 | 19.36 | 17.18 | 14.94 | 11.79 |
| 30 | 20:0 | 0.38 | 0.31 | 0.28 | 0.29 |
| 31 | cct-18:3 | 0.24 | 0.05 | 0.13 | −0.01 |
| 32 | 9c-20:1, ctc | 0.13 | 0.08 | 0.09 | 0.01 |
| 33 | 10c-20:1, cct | 0.18 | 0.02 | 0.14 | −0.04 |
| 34 | 11c-20:1 | 0.31 | 0.15 | 0.65 | 0.34 |
| 35 | 18:3n3 | 1.00 | 2.65 | 0.73 | 1.39 |
| 36 | 9c11t-CLA | 0.14 | 0.12 | 0.08 | 0.07 |
| 37 | 20:2n6 | 0.12 | 0.08 | 0.43 | 0.34 |
| 38 | 22:0 | 0.27 | 0.21 | 0.09 | 0.08 |
| 39 | 24:0 | 0.09 | 0.08 | 0.02 | 0.04 |
| 40 | T Sat | 29.17 | 29.28 | 36.41 | 39.37 |
| 41 | T C MUFA | 33.08 | 33.79 | 39.05 | 38.45 |
| 42 | T C PUFA | 20.48 | 19.92 | 16.10 | 13.36 |
| 43 | T MUFA trans | 11.40 | 13.48 | 4.07 | 6.21 |
| 44 | T DUFA trans | 3.57 | 2.39 | 1.33 | 0.73 |
| 45 | T TUFA trans | 0.55 | 0.15 | 0.36 | −0.05 |
| 46 | T Trans | 15.51 | 16.13 | 5.76 | 6.85 |

GC-HPLC = Gas Chromatography High Performance Liquid Chromatography
FT-NIR = Fourier Transform Near Infrared Spectroscopy

TABLE 8

Comparison of GC and FT-NIR results for extracted fish oil

| No. | Fatty cid | Herring Oil GC | Herring Oil FT-NIR |
|---|---|---|---|
| 1 | 14.00 | 4.41 | 4.55 |
| 2 | 15:0 | 0.26 | 0.26 |
| 3 | 16:00 | 7.93 | 7.83 |
| 4 | 16:01 | 8.34 | 8.29 |
| 5 | 11c-16:1 | 0.23 | 0.22 |
| 6 | T 17:1 | 0.26 | 0.26 |
| 7 | 16:2n3 | 0.62 | 0.63 |
| 8 | 18:00 | 0.67 | 0.57 |
| 9 | 16:3n-3 | 0.65 | 0.66 |
| 10 | 16:3n-3 | 0.48 | 0.48 |
| 11 | Cis 9 18:1 | 3.91 | 3.85 |
| 12 | Cis 1118:1 | 1.75 | 1.72 |
| 13 | 13c- | 0.53 | 0.53 |
| 14 | 19:00 | 0.03 | 0.02 |
| 15 | 16:4n3 | 1.02 | 1.00 |
| 16 | 18:2 n6 | 0.60 | 0.62 |
| 17 | 18:2 n? | 0.11 | 0.11 |
| 18 | 20:00 | 0.25 | 0.24 |
| 19 | 18:3n-6 | 0.08 | 0.08 |
| 20 | 20:1 n-9 | 1.77 | 1.78 |
| 21 | 20:1 n-7 | 18.21 | 18.10 |
| 22 | 18:3 n3 | 0.27 | 0.31 |
| 23 | 18:4 n-3 | 1.40 | 1.36 |
| 24 | 18:4n-6 | 0.11 | 0.11 |
| 25 | 18:4n-3 | 0.93 | 1.01 |
| 26 | 20:2 n-6 | 0.01 | 0.01 |
| 27 | 22:0 | 0.19 | 0.19 |
| 28 | 11c-22:1 | 28.54 | 28.69 |
| 29 | 22:1 n-9 | 3.06 | 3.04 |
| 30 | 20:3 n-3 | 0.54 | 0.54 |
| 31 | 20:4 n-6 | 0.10 | 0.06 |
| 32 | 20:4 n-3 | 0.21 | 0.21 |
| 33 | 22:2 n-6 | 0.14 | 0.14 |
| 34 | 20:5 n-3 | 4.84 | 4.57 |
| 35 | 24:1n11 | 0.14 | 0.17 |
| 36 | 24:1? | 0.15 | 0.14 |
| 37 | 15c-24:1 | 0.51 | 0.52 |
| 38 | 24:2? | 0.18 | 0.18 |
| 39 | 22:5n6 | 0.01 | 0.02 |
| 40 | 22:5 n-3 | 0.68 | 0.78 |
| 41 | 22:6n-3 | 2.07 | 2.27 |
| 42 | Total FA | 96.22 | 96.10 |

I claim:

1. A method for the determination of the fatty acid type and content of a fat or oil component of a material comprising:
   analyzing the fatty acid type and quantity of a baseline composition using a fatty acid reference analytical technique;
   analyzing the fatty acid type and quantity of said baseline composition using a Fourier Transform-Near Infrared (FT-NIR) analysis technique;
   preparing a calibration matrix by comparing results from said fatty acid reference analytical technique to the results from said FT-NIR analysis technique;
   analysing the material using an FT-NIR technique; and
   identifying and quantifying the type and content of fatty acids present in the material by comparing spectral data obtained from said FT-NIR technique of the material to said calibration matrix.

2. A method as claimed in claim 1 wherein said calibration matrix is prepared using a technique based on data obtained by GC and FT-NIR analysis of selected baseline materials.

3. A method as claimed in claim 2 wherein said baseline composition is similar in composition, with respect to the type of fatty acid, to the material but has a range of fatty acid levels.

4. A method as claimed in claim 2 wherein said calibration matrix is based on a statistical analysis of FT-NIR spectral data and GC data obtained from the analysis of said baseline composition.

5. A method as claimed in claim 4 wherein said statistical analysis involves multiple linear regression (MLR), principal component regression (PCR), or partial least squares regression (PLSR).

6. A method as claimed in claim 1 wherein said FT-NIR technique uses a near-infrared region of the spectrum that has a frequency range of from between 4000 $cm^{-1}$ (2.5 microns) and 14000 $cm^{-1}$ (0.7 microns) wavenumber.

7. A method as claimed in claim 1 wherein said FT-NIR technique for analyzing said material is based on a reflective technique, transmission technique and/or transflectance technique.

8. A method as claimed in claim 1 wherein said material is a food product.

9. A method as claimed in claim 1 wherein said material is vegetable oil, soy oil, flax oil, fish oils or oils extracted from fish, shortening, lard, mayonnaise, salad dressing, cookies, baked goods, crackers or potato chips.

10. A method as claimed in claim 1 wherein said material is tested to determine the level of trans fatty acids in the material.

11. A method as claimed in claim 1 wherein said material is fish oil or oils extracted from fish.

12. A method as claimed in claim 1 wherein said material is analyzed to determine the level of Omega-3(LC) PUFAs (polyunsaturated fatty acids) in the material.

13. A method as claimed in claim 12 wherein said Omega-3(LC) PUFA is EPA (eicosapentaenoic acid) or DHA (decosahexaenoic acid).

14. A method as claimed in claim 1 wherein said material is living tissue.

15. A method as claimed in claim 14 wherein said living tissue is human tissue, fish tissue, or non-human mammal tissue.

16. A method as claimed in claim 1 wherein said FT-NIR analysis involves use of mathematically modified values to improve the ability to distinguish one material over another.

17. A method as claimed in claim 1 wherein the fat or oil of said material is extracted prior to FT-NIR analysis.

18. A method as claimed in claim 1 wherein all FT-NIR analysis is conducted at a pre-determined temperature.

19. A method as claimed in claim 1 wherein said FT-NIR analysis is conducted at different temperatures in order to obtain FT-NIR spectral data at different temperatures and thus provide spectral data having a temperature variability, and modification of said calibration matrix to account for the temperature variability encountered during analysis of the material.

20. A method as claimed in claim 1 wherein the FT-NIR analysis of said material is conducted in a time of less than 2 minutes.

21. The method of claim 1, wherein the calibration matrix is obtained from any analytical technique which can directly or indirectly provide specific information on the type and quantity of the fatty acid components of a fat or oil.

22. The method of claim 21, wherein the analytical technique comprises a GC-based procedure.

23. The method of claim 22, wherein the GC-based procedure is standard GC, GC Silver Ion, GC-HPLC, GC-TLC or GC-MS.

24. A method for the determination of the fatty acid type and content of a fat or oil component of a material comprising:
   analyzing the fatty acid type and quantity of a baseline composition using a fatty acid reference analytical technique;
   analyzing the fatty acid type and quantity of said baseline composition using a Fourier Transform-Near Infrared (FT-NIR) analysis technique;
   preparing a calibration matrix by comparing results of said fatty acid reference analytical technique to the results from said FT-NIR analysis technique;
   analysing the material using an FT-NIR technique; and
   identifying and quantifying the type and content of two or more fatty acids present in the material by comparing spectral data obtained from said FT-NIR technique of the material to said calibration matrix.

* * * * *